(12) United States Patent
Jacobs et al.

(10) Patent No.: US 6,516,817 B2
(45) Date of Patent: Feb. 11, 2003

(54) MONITORING OF CLEANING PROCESS

(76) Inventors: Paul T. Jacobs, 8 Rainier, Trabuco Canyon, CA (US) 92679; Jenn-Han Wang, 21622 Marguerita Pkwy. Apt# 341, Mission Viejo, CA (US) 92692; Szu-Min Lin, 25632 Rain Tree Rd., Laguna Hills, CA (US) 92653

( * ) Notice: Subject to any disclaimer, the term of this patent is extended or adjusted under 35 U.S.C. 154(b) by 0 days.

(21) Appl. No.: 09/871,219

(22) Filed: May 31, 2001

(65) Prior Publication Data

US 2001/0033805 A1 Oct. 25, 2001

Related U.S. Application Data

(62) Division of application No. 09/075,714, filed on May 11, 1998, now Pat. No. 6,394,111.
(60) Provisional application No. 60/049,351, filed on Jun. 11, 1997.

(51) Int. Cl.[7] .................................................. B08B 3/04
(52) U.S. Cl. ................. 134/113; 134/58 R; 134/166 R; 134/166 C; 134/200
(58) Field of Search .............................. 134/116 R, 113, 134/56 R, 58 R, 200, 166 C; 68/12.02; 435/287.4; 422/28

(56) References Cited

U.S. PATENT DOCUMENTS

| | | | |
|---|---|---|---|
| 3,276,458 A | * | 10/1966 | Iversen et al. |
| 3,640,295 A | | 2/1972 | Peterson |
| 3,657,073 A | | 4/1972 | Burton et al. |
| 3,861,875 A | * | 1/1975 | Joslyn |
| 3,957,252 A | | 5/1976 | Storz |
| 3,982,893 A | * | 9/1976 | Joslyn |
| 4,064,886 A | | 12/1977 | Heckele |
| 4,311,793 A | * | 1/1982 | Halleck |
| 4,591,566 A | * | 5/1986 | Smith |
| 4,592,785 A | | 6/1986 | Reinert et al. |
| 4,710,233 A | | 12/1987 | Hohmann et al. |
| 4,743,537 A | | 5/1988 | McCormick et al. |
| 4,850,716 A | * | 7/1989 | Baker et al. |
| 4,863,867 A | | 9/1989 | Joyce et al. |
| 5,032,186 A | | 7/1991 | Childers et al. |
| 5,048,139 A | | 9/1991 | Matsumi et al. |
| 5,122,344 A | * | 6/1992 | Schmoegner |
| 5,140,842 A | * | 8/1992 | Kiuchi et al. |
| 5,259,219 A | * | 11/1993 | Dausch et al. |
| 5,277,875 A | | 1/1994 | Albright et al. |
| 5,291,626 A | * | 3/1994 | Molnar et al. |
| 5,396,178 A | * | 3/1995 | Rybarski |
| 5,405,587 A | | 4/1995 | Fernandez et al. |

(List continued on next page.)

FOREIGN PATENT DOCUMENTS

| | | |
|---|---|---|
| DE | 44 37 103 A1 | 4/1996 |
| DE | 196 02 673 A1 | 8/1997 |
| GB | 2 248 188 A | 4/1992 |
| WO | WO 97/27482 | 7/1997 |

*Primary Examiner*—Frankie L. Stinson
(74) *Attorney, Agent, or Firm*—Knobbe, Martens, Olson & Bear, LLP

(57) ABSTRACT

A method for monitoring a cleaning process for a soiled medical device. The method involves cleaning the soiled device with a cleaning liquid in a cleaning chamber, exposing a detector to the cleaning liquid to measure the amount of soil removed, determining whether a sufficient amount of the soil has been removed from the soiled device so that the soiled device can be sterilized, and sterilizing the soiled device. One method of determining the amount of soil is by detecting the signal generated from the reaction between a chemical and the soil. Another method is to provide a soiled standard and measure the amount of soil removed from the soiled standard to determine whether enough soil has been removed from the soiled standard so that the soiled device can be sterilized. Another method involves measuring the amount of soil removed from the soiled device with at least two detectors.

16 Claims, 18 Drawing Sheets

U.S. PATENT DOCUMENTS

| | | | |
|---|---|---|---|
| 5,411,042 A | * | 5/1995 | Suzuki et al. |
| 5,422,276 A | * | 6/1995 | Colvin |
| 5,424,939 A | * | 6/1995 | Kweon |
| 5,445,792 A | * | 8/1995 | Rickloff et al. |
| 5,446,531 A | | 8/1995 | Oyer et al. |
| 5,491,092 A | * | 2/1996 | Colvin |
| 5,535,141 A | | 7/1996 | Lüssi |
| 5,558,841 A | | 9/1996 | Nakagawa et al. |
| 5,565,634 A | * | 10/1996 | Graessle et al. |
| 5,647,386 A | * | 7/1997 | Kaiser |
| 5,711,921 A | | 1/1998 | Langford |
| 5,722,441 A | * | 3/1998 | Teramoto |
| 5,736,355 A | | 4/1998 | Dyke et al. |
| 5,747,794 A | | 5/1998 | Malchesky |
| 5,753,195 A | | 5/1998 | Langford et al. |
| 5,788,925 A | * | 8/1998 | Pai et al. |
| 5,830,683 A | | 11/1998 | Hendricks et al. |
| 5,834,313 A | | 11/1998 | Lin |
| 5,863,790 A | | 1/1999 | Bolea |
| 5,882,590 A | * | 3/1999 | Stewart et al. |
| 5,906,802 A | | 5/1999 | Langford |
| 5,923,432 A | * | 7/1999 | Kral |
| 5,928,948 A | | 7/1999 | Malchesky |
| 5,960,804 A | * | 10/1999 | Cooper et al. |
| 6,107,097 A | | 8/2000 | Pfeifer |
| 6,193,931 B1 | | 2/2001 | Lin et al. |

* cited by examiner

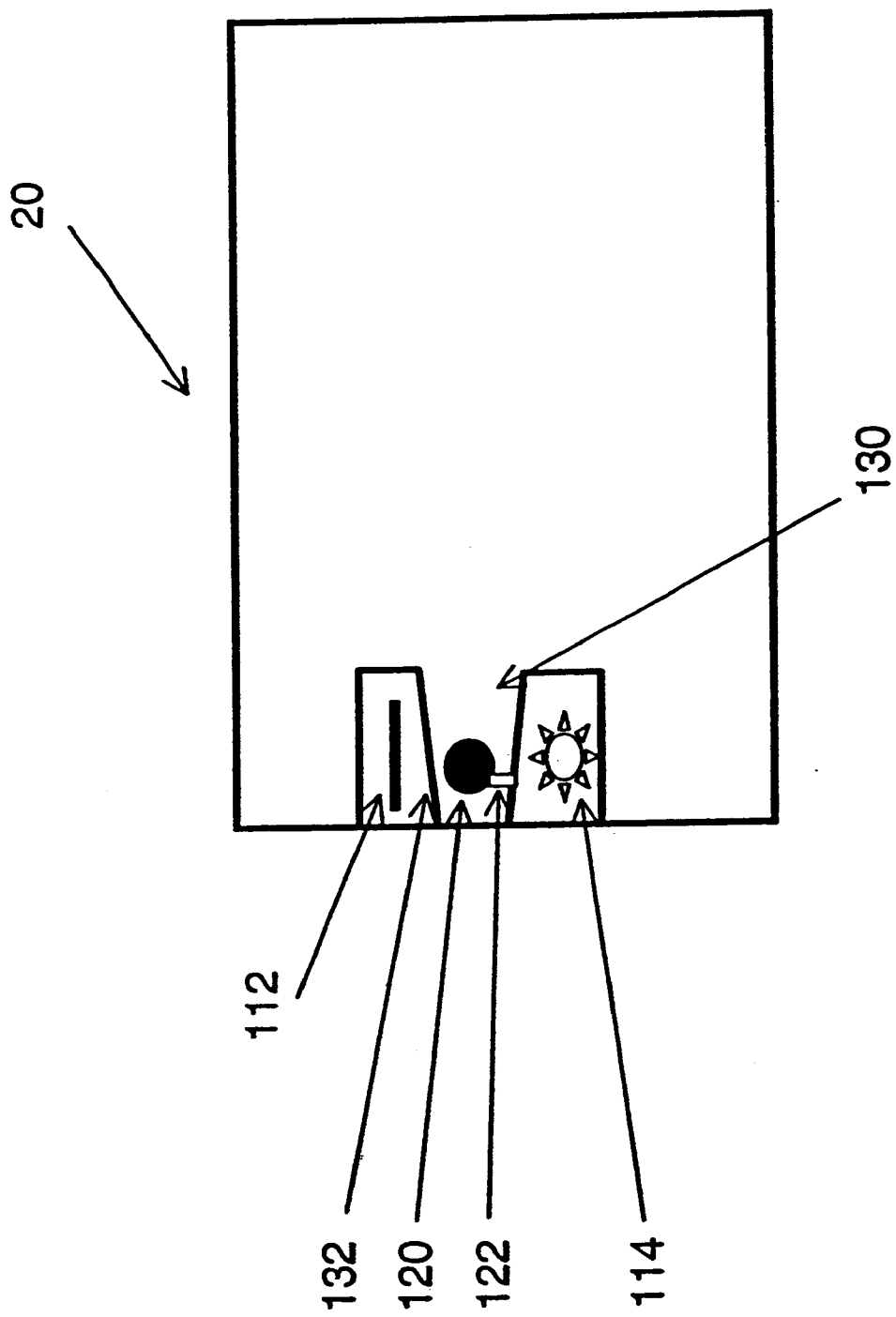

MONITORING OF CLEANING PROCESS

RELATED APPLICATIONS

This application is a divisional of prior application Ser. No. 09/075,714, filed on May 11, 1998, now U.S. Pat. No. 6,394,111, which claims the benefits of Provisional Application Ser. No. 60/049,351, entitled "DETECTION OF CLEANLINESS OF A MEDICAL DEVICE DURING A WASHING PROCESS", filed on Jun. 11, 1997.

BACKGROUND OF THE INVENTION

1. Field of the Invention

This invention relates to an apparatus and method for monitoring cleaning processes for medical devices. More particularly, this invention relates to an apparatus and method capable of determining when the device is sufficiently cleaned so that the device can be sterilized.

2. Description of the Related Art

Adequate cleaning of contaminated medical instruments and devices is essential for safe disinfection and sterilization. Failure to adequately remove inorganic and organic soil derived from body liquids and tissues can impede the effectiveness of subsequent sterilization procedures resulting in infections. Additionally, remaining foreign materials introduced during subsequent invasive procedures can produce pyrogenic reactions that can impede healing.

It is preferable to use machine processes for cleaning which have been validated for this purpose in a clinical setting and which preferably accomplish sterilization during or after the cleaning cycle. The selected cleaning processes should produce satisfactory results under certain test and field conditions as well as ensure that adequate cleaning is performed under exceptional circumstances and conditions.

It is not only necessary that a high level of cleaning performance be achieved, but also that the cleaning system be capable of adapting to the specific needs of particular medical instruments and devices. The ideal cleaning system will be capable of adequately cleaning medical instruments and devices with long, narrow, inaccessible orifices such as those found on flexible endoscopes as well as the inner surfaces of take-apart, modular instruments. In the case of sophisticated instruments which may no longer be able to be taken apart in the future, adequate cleaning performance must also be achieved.

A variety of cleaning machines and related apparatus have been developed for medical instruments and devices.

U.S. Pat. No. 3,640,295 to Peterson describes an ultrasonic cleaner and surgical instrument carrying case, which is useable separately and apart from or in combination with the ultrasonic cleaner, the ultrasonic cleaner including within at least one sink and oscillatable cradle which may carry the instrument case during the ultrasonic cleaning process. A pump and filter are additionally provided as part of the ultrasonic cleaner to circulate a cleaning fluid within the sink of the ultrasonic cleaner and to remove particles and other matter from the fluid. The Peterson '295 patent does not address standards or quality of cleaning.

U.S. Pat. No. 3,957,252 to Storz and assigned to Storz-Endoskop GmbH discloses an apparatus for cleaning medical instruments. The apparatus disclosed in the '252 Storz patent pertains to support means provided for mounting an ultrasonic oscillator for engaging washing water in a conventional sink, for use in cleaning medical instruments. The focus of the invention is to eliminate the need for an independent special ultrasonic cleaning tank.

U.S. Pat. No. 4,064,886 to Heckele and assigned to Riwoplan Medizin-Technische Einrichtungs-Gesellschaft GmbH discloses an apparatus for cleaning endoscopes, comprising a holder device, a cylindrical cleaning container, time control means for placing the holder device under timed control and a rotatable mounting for the holder device. The object of the invention is to enable fast and automatic cleansing and sterilization of endoscopes, which can be carried out without damaging the endoscopes. Again, the invention does not address standards or quality of cleaning.

U.S. Pat. No. 4,710,233 to Hohmann et al. and assigned Siemens Aktiengesellschaft discloses a method and apparatus for cleaning, disinfecting, and sterilizing medical instruments with a sequence of method steps performed in a single apparatus. The invention discloses a complicated method and apparatus. The method steps include precleaning the instruments in a container containing a first fluid bath subjected to ultrasonic energy for a period of time T1, subsequently emptying the first fluid bath from the container and replacing it with a second fluid bath containing a cleaning agent and sodium chloride, fine cleaning and disinfecting the instruments by subjecting the second bath to ultrasonic energy for a time period T2 and circulating the second bath through an electrolytic cell having a voltage applied to the electrodes to create an electrolytic disassociation therein, then emptying the second bath and replacing it with a rinse bath, rinsing instruments for a time period T3 by subjecting the rinsing bath to ultrasonic energy and circulating the rinsing bath through the electrolytic cell subsequently emptying the rinse bath, and drying the instruments by means of heated air. Thus, the Hohmann '233 invention is designed to provide adequate cleaning and sterilization of medical instruments, however, this is achieved with an expensive and complicated apparatus and method.

U.S. Pat. No. 5,032,186 to Childers, et al. and assigned to American Sterilizer Company discloses a method and apparatus for washing and sterilizing hospital or laboratory materials. The invention involves loading a chamber with items to be washed, filling the chamber to a predetermined level with a washing fluid, controllably injecting a steam or an air-steam mixture into the chamber during the filling of a chamber with the washing fluid, the steam being injected in a turbulent manner to create a washing action and to begin heating the washing fluid, and continually injecting steam into the chamber after the chamber is filled to the predetermined level so as to subject the items to a washing action. After the washing phase, the chamber is drained, the items are rinsed and the chamber is drained again. Sensors are employed to monitor the operating parameters of the apparatus. Sensors are utilized for controlling the operation of the spray nozzles and the steam injectors such that steam is controllably injected into the chamber after a certain point during the filling of the chamber with the washing fluid to create a washing action and to begin heating the washing fluid. Again, this invention does not provide means to assure adequacy of cleaning.

U.K. Patent Application No. 2,248,188 A to Parker, et al. and assigned to Keymed Ltd. discloses a method and apparatus for cleaning and disinfecting medical instruments. The method and apparatus of the invention are particularly suited for cleaning and disinfecting endoscopes. The method comprises the steps of placing an instrument in an enclosure and subjecting the instrument to a cleaning phase in which a cleansing solution is applied to the surfaces of the instruments, a disinfection phase in which a disinfectant solution is applied to the surfaces of the instrument, a rinsing phase in which a flushing solution is applied to the surfaces of the instrument, a purging phase in which a volatile liquid is applied to the surfaces of the instruments and a drying phase in which a drying gas is passed over the surfaces of the instrument. The cleaning phase is described as a period sufficient to thoroughly clean the endoscope both externally and internally. Again, the invention does not address means for assuring adequacy of cleaning.

None of the aforementioned apparatus and methods provide the means for assuring adequacy of cleaning of a medical device or instrument. Therefore, a need remains for an improved apparatus and method for monitoring cleaning processes for medical devices.

SUMMARY OF THE INVENTION

Before a detailed discussion of the present invention is given, it should be mentioned that certain terms have been used in this disclosure in their broadest meaning. Thus, the term "sterilization" or "sterilize" as used herein also include the meaning of disinfection. Similarly, the terms "cleaning" and "cleaning liquid" as used herein also cover rinsing or a rinsing liquid.

The invention relates to an apparatus and method for monitoring a cleaning process for a medical device, capable of determining when the device is sufficiently clean so that the device can be sterilized.

A soil detector is provided in the apparatus of the invention, which may utilize a variety of detection technologies for monitoring cleaning, alone or in combination. Generally, the detection technology is selected from the group consisting of ion-selective electrodes, conductivity, spectrophotometry, ion chromatography, capillary electrophoresis, high performance liquid chromatography, liquid chromatography, cyclic voltammetry, radioactivity, quartz crystal microbalance and other gravimetric techniques, infra-red spectroscopy and other spectroscopic techniques.

The apparatus of the invention may employ detection technology wherein the detection technology is suitable for detecting the presence of the soil on a surface of a medical device. The detection technology which is suitable for detecting the presence of soil on a surface of a medical device may operate without contacting the surface of the device. Alternatively, detection technology suitable for detecting the presence of soil on the surface of a medical device may operate via direct surface contact. Alternatively, an indirect detection technology may also be employed. This approach employs the same physical-chemical detection technologies previously mentioned for other approaches. However, the medical device itself is not monitored for the degree of cleaning. Rather, a soil-deposited standard is inserted in the apparatus and monitored in place of the medical device itself. A correlation between the degree of cleaning of the soiled device to be cleaned and the degree of cleaning of the soiled standard can be established, so that when the standard is cleaned to certain degree the sufficient cleaning of the device to be cleaned is achieved.

Thus, in one aspect of the present invention, there is provided an apparatus for monitoring a cleaning process for a medical instrument. The apparatus comprises a cleaning chamber for receiving and cleaning the instrument with a cleaning liquid. A soil detector is coupled to the cleaning chamber and adapted to provide an indication of the amount of the soil on the instrument. The soil detector is at least partially isolated from the chamber so that access to the detector by the cleaning liquid is controllable. The soil detector can be moveable, and by moving the detector it can be made in or out of fluid communication with the chamber. The soil detector may comprise an electrode located in an enclosure, and the enclosure is so coupled to the chamber that the cleaning liquid has controllable access to the enclosure.

In another aspect of the present invention, there is provided a method for cleaning and sterilizing a soiled medical device. The method comprises the steps of: a) providing a cleaning chamber for receiving the soiled device; b) providing a soil detector coupled with the cleaning chamber; c) introducing a cleaning liquid into the cleaning chamber; d) cleaning the soiled device in the cleaning chamber; e) exposing the detector to the cleaning liquid so as to measure the amount of soil removed from the soiled device; f) determining that a sufficient amount of the soil has been removed from the soiled device so that the soiled device can be sterilized; and g) sterilizing the soiled device. Preferably, the detector is at least partially obstructed from the cleaning liquid during step d). Exposing the detector to the cleaning liquid and obstructing the detector from the cleaning liquid can be achieved by moving the detector in and out of fluid communication with the chamber, or by locating the detector in an enclosure so coupled to the chamber that the cleaning liquid has controllable access to the enclosure.

In another aspect of the present invention, there is provided an apparatus for monitoring a cleaning process for a soiled medical instrument. The apparatus comprises a chamber for receiving and cleaning the instrument. An enclosure is in controllable fluid communication with the chamber. A chemical source is coupled to the enclosure for providing a chemical capable of reacting with the soil of the instrument to generate a detectable signal in the enclosure. A detector for detecting the signal is provided with the apparatus. The chemical can be selected from $Hg(SCN)_2$, OPA(o-phthatic dialdehyde+Triol), Bromcresol purple ($C_{12}H_{16}Br_2O_5S_9$), biuret reagent, and Microprotein-PR. The apparatus may further comprise a light source for sending a light beam through the cleaning liquid in the enclosure to the detector. The enclosure may be separated from the chamber by a valve. The chamber has an inlet and an outlet, and a second detector can be coupled to the inlet, and the first detector and the enclosure are coupled to the outlet.

In another aspect of the present invention, there is provided a method for cleaning and sterilizing a soiled medical device. The method comprises the steps of: a) providing a cleaning chamber for receiving the soiled device; b) providing a chemical source coupled to an enclosure in controllable fluid communication with the cleaning chamber, the source containing a chemical capable of reacting with the soil on the device to generate a detectable signal; c) introducing a cleaning liquid into the cleaning chamber; d) cleaning the soiled device in the cleaning chamber; e) releasing the chemical from the source into the enclosure; f) detecting the signal generated through reaction between the chemical and soil in the cleaning fluid to determine if a sufficient amount of soil has been removed form the device; and g) sterilizing the device. A portion of the cleaning fluid can be introduced into the enclosure before the chemical is released into the enclosure, and before the introduction of the portion of the cleaning liquid, the enclosure can be separated from the cleaning chamber so that substantially there is no fluid communication therebetween. The signal can be color or absorption at certain wave length.

In another aspect of the present invention, there is provided an apparatus for monitoring a cleaning process for a medical instrument. The apparatus comprises a chamber for receiving and cleaning the instrument. A standard containing a predetermined amount of soil is positioned in the chamber or in controllable fluid communication with the chamber. A detector adapted to provide an indication of the amount of the soil on the standard is coupled to the apparatus. The apparatus may comprises a cleaning/rinsing system which is adjustable so as to change relative cleaning efficiency in different locations of the apparatus. The standard can be positioned so that the instrument is cleaned more efficiently than the standard. The indication can be a signal such as concentration of the soil in a liquid used to clean the device, electrical potential of a liquid used to clean the device, conductivity, transparency to certain wave length, or color of a liquid used for the cleaning. Preferably, the standard may comprise a surface covered with the soil. An additional light source may be provided which generates a light beam of a predetermined wave length which travels through the standard and reaches the detector. The standard can be placed in an enclosure in controllable fluid communication with the chamber. The enclosure can be provided with a chemical source capable of controllably releasing a chemical to the enclosure, which chemical reacts with the soil removed from or remained on the standard to generate a detectable signal. The detector may comprise an electrode located in the enclosure.

In another aspect of the present invention, there is provided a method for cleaning and sterilizing a soiled medical device. The method comprises the steps of: a) providing a chamber for receiving the soiled device; b) providing a soiled standard coupled to the chamber; c) introducing a cleaning liquid into the chamber; d) cleaning the soiled device and the soiled standard; e) measuring the amount of soil removed from the soiled standard; f) determining that a sufficient amount of the soil has been removed from the soiled standard so that the soiled device can be sterilized; and g) sterilizing the soiled device. Preferably, the cleaning step comprises exposing the standard to a cleaning environment as effective or less effective than that to which the soiled device is exposed, and the determining step comprises determining that the soiled standard has been cleaned to a predetermined level. The soiled standard can be more heavily soiled or more difficult to clean than the soiled device. The method may further comprise measuring soil level of the cleaning liquid before the liquid is introduced into the chamber. Step e) may comprise measuring an inorganic soil such as inorganic electrolytes, alkaline and alkaline earth salts, inorganic metal-containing compounds and other inorganic compounds present in the human body which may come in contact with a medical device, and/or measuring an organic soil such as proteins, glycoproteins, lipoproteins, mucous, amino acids, polysaccharides, sugars, lipids, glycolipids, other organic compounds present in the human body which may come in contact with a medical device, microorganisms and viruses. The step of measuring the amount of soil removed from the soiled device can be conducted by detecting soil remained on the soiled standard or soil removed from the soiled standard and contained in the cleaning liquid. Preferably, the soiled standard is placed in an enclosure in controllable fluid communication with the chamber, so that by controlling the degree of fluid communication between the chamber and the enclosure, the relative cleaning efficiency of the chamber and the enclosure can be adjusted. Step e) may comprise measuring the soil level of the cleaning liquid in the enclosure.

In another aspect of the present invention, there is provided an apparatus for monitoring a cleaning process for a medical instrument. The apparatus comprises a cleaning chamber for receiving and cleaning the instrument, and at least a first soil detector and a second soil detector adapted to provide an indication of the amount of soil removed from or remained on the instrument. The first and second soil detectors are placeable in fluid communication with the cleaning chamber. The first and the second soil detectors may be selected from ion-selective electrodes, conductivity, spectrophotometry, ion chromatography, capillary electrophoresis, high performance liquid chromatography, liquid chromatography, radioactivity, gravimetry, infra-red spectroscopy, potentiometry and turbidimetry. One of the soil detectors may be adapted to detect inorganic soil, and the other to detect organic soil. One detector can be located adjacent to an inlet of the cleaning chamber, and the other detector is located adjacent to an outlet of the cleaning chamber. The apparatus may further comprise a second chamber in fluid communication with the cleaning chamber, and one detector is located in the second chamber, one in the cleaning chamber, so that the measuring results from the two chambers can be compared and used to determine the degree of cleaning.

In still another aspect of the present invention, there is provided a method for cleaning and sterilizing a soiled medical device. The method comprises the steps of: a) providing a cleaning chamber for receiving the soiled device; b) introducing a cleaning liquid into the cleaning chamber; c) cleaning the soiled device in the cleaning chamber; d) measuring the amount of soil removed from the soiled device with at least two detectors; e) determining that a sufficient amount of the soil has been removed from the soiled device so that the soiled device can be sterilized; and f) sterilizing the device. Step d) may comprise measuring soil level of the cleaning liquid with a first detector before the cleaning, and measuring the soil level of the cleaning liquid with a second detector during or after cleaning. Step e) may comprise comparing the soil level of the cleaning liquid measured by the first detector with the soil level of the cleaning liquid measured by the second detector. If the difference between the two soil levels is within a predetermined range, the sufficient amount of soil has been removed from the soiled device. Step d) may comprise measuring, with one detector, an inorganic soil such as inorganic electrolytes, alkaline and alkaline earth salts, inorganic metal-containing compounds and other inorganic compounds present in the human body which may come in contact with a medical device, and measuring, with another detector, an organic soil such as proteins, glycoproteins, lipoproteins, mucous, amino acids, polysaccharides, sugars, lipids, glycolipids, other organic compounds present in the human body which may come in contact with a medical device, microorganisms and viruses. The step of measuring the amount of soil removed from the soiled device may be conducted by detecting soil remained on the soiled device or soil removed from the soiled device and contained in the cleaning liquid.

The apparatus of the present invention as discussed above may further comprise a vacuum pump connected to the chamber, so that the chamber also functions as a vacuum chamber.

The apparatus of the present invention as discussed above may further comprises a sterilization system.

In the method according to the present invention, the sterilizing step can be conducted by a vapor phase procedure.

In the method according to the present invention, the cleaning liquid can comprise a liquid sterilization agent, such that the cleaning step and the sterilizing step are conducted simultaneously.

The method according to the present invention may further comprise a vacuum drying step.

BRIEF DESCRIPTION OF THE DRAWINGS

FIGS. 15a–15d are schematic diagrams of the apparatus according to another embodiment of the invention, which has a standard covered with soil.

DETAILED DESCRIPTION OF THE PREFERRED EMBODIMENT

Figure 1:
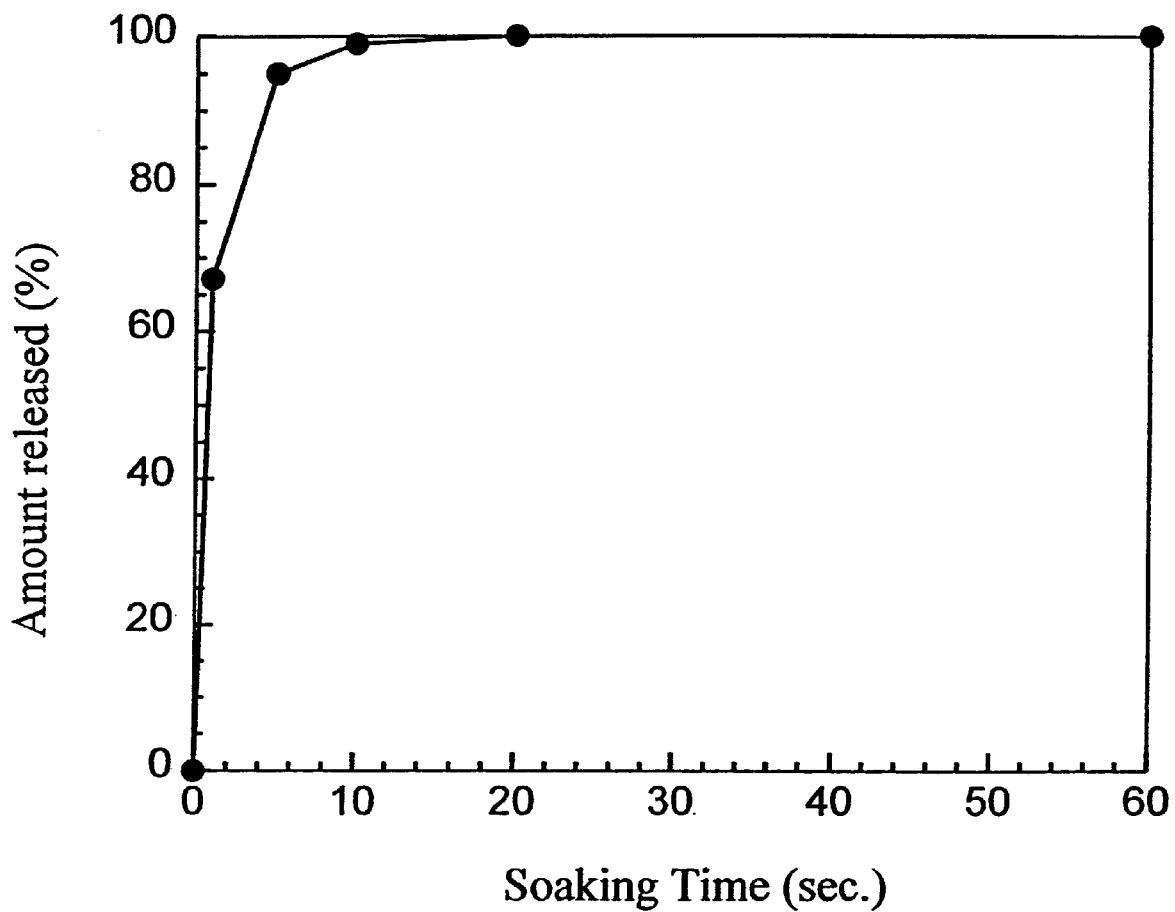
FIG. 1 is a graph of the sodium chloride release rate of sodium chloride inoculated stainless steel blades in deionized water at room temperature.

One aspect of the present invention is to determine when a medical device is sufficiently cleaned so that one can insure that a subsequent sterilization process will provide a sterile product, such as one having sterility assurance level (SAL) of $10^{-6}$. That is, the probability of having a non-sterile device is less than one in one million. In order to develop technologies capable of accomplishing the above objective, studies were conducted to elucidate some of the important relationships between surface contamination with microorganisms, surface deposit type and subsequent sterilization of medical devices.

The first experiment involved the inoculation of one million *Bacillus stearothermophilus* (Bst) spores in various concentrations of saline (sodium chloride) in 100 microliters of water onto stainless steel blades. Twenty blades were utilized for each concentration of saline solution evaluated. Following drying overnight, the blades were subjected to a standard sterilization protocol for one cycle of sterilization in a commercially available sterilization apparatus from Advanced Sterilization Products in Irvine, Calif. The sterilization protocol included double wrapping the blades in CSR wrap and utilizing a full sterilization cycle with 6 mg/liter of hydrogen peroxide in the chamber delivered from a 59% hydrogen peroxide solution. The blades were then placed into a TSB culture medium and incubated at 55° C. for 14 days to determine if any viable organisms were remaining. Each concentration of saline was evaluated with three replicates, with a total of 60 blades. The following are the results:

TABLE 1

Range Finding: $10^6$ Bst. spores in various concentrations of saline in Water
100 μl inoculated onto stainless steel blades.

| Total % weight of NaCl in water | .85% | .17% | .034% | .0068% |
|---|---|---|---|---|
| Trial 1 | 20/20 | 13/20 | 4/20 | 5/20 |
| Trial 2 | 20/20 | 16/20 | 8/20 | 2/20 |
| Trial 3 | 20/20 | 18/20 | 5/20 | 4/20 |
| Total | 60/60 | 47/60 | 17/60 | 11/60 |

The first number in each column represents the number of blades found to contain viable organisms following exposure to the sterilization process. The second number in each column represents the number of blades evaluated in each trial. It can be seen that as the amount of saline in the surface deposit decreases, the fewer the number of viable remaining organisms and hence the more efficient the sterilization process. Similar experiments were conducted with a surface deposit comprised of various concentrations of Fetal Bovine Serum (FBS), which naturally contains approximately 0.75% of salt when undiluted as well as a surface deposit comprised of various amounts of saline along with various amounts of Fetal Bovine Serum. The results of those experiments follow:

TABLE 2

Range Finding: $10^6$ Bst. spores in various concentrations of Fetal Bovine Serum
100 μl inoculated onto stainless steel blades.

| % NaCl in PBS | .75% | .15% | .03% | .006% | 0% |
|---|---|---|---|---|---|
| % PBS in DI water | 100% | 20% | 4% | .8% | 0% |
| Trial 1 | 1/20 | 0/20 | 0/20 | 0/20 | 0/10 |
| Trial 2 | 0/20 | 0/20 | 0/20 | 0/20 | 0/10 |
| Trial 3 | 0/20 | 0/20 | 0/20 | 0/20 | 0/10 |
| Total | 1/60 | 0/60 | 0/60 | 0/60 | 0/30 |

It can be seen that a surface deposit comprised solely of Fetal Bovine Serum provides virtually no interference with subsequent sterilization in this particular experiment protocol even though it contains 0.75% salt when undiluted. It is believed that the presence of protein in the serum prevents the formation of salt crystals during the drying process. These salt crystals may occlude microorganisms and protect them from sterilization processes. Therefore, the presence of salts, such as NaCl, in surface deposits on medical devices, present a special challenge in terms of obtaining a sterile device during a concurrent or subsequent sterilization process. Since it is an objective of the present invention to determine when medical devices are clean enough to be sterilized, the monitoring of salt concentration during the washing process is of great importance. Nevertheless, tap water which contains multiple salts at relatively low concentration presents less of a challenge because uniform crystals are unlikely to form.

Additional experiments simulating rinsing or cleaning processes were conducted on soil-deposited stainless steel (SS) blades or polytetrafluoroethylene (PTFE) plastic strips as models for stainless steel and plastic medical devices and instruments. These experiments elucidate some of the important relationships between surface deposit (or soil) type and release or cleaning rates during a simulated rinsing or cleaning process.

A series of soil-containing solutions were prepared with compositions as illustrated in Table 3.

TABLE 3

| Solution | NaCl | albumin | proteins, total | Water |
| --- | --- | --- | --- | --- |
| NaCl solution | 0.74% | 0 | 0 | 99.26% |
| Albumin solution | 0.73% | 4.20% | 4.20% | 95.07% |
| RPMI + 10% FBS | 0.75% | | 0.35% | |
| Fetal bovine serum | 0.70% | 2.20% | 3.51% | |

RPMI tissue culture medium, which is known in the art, when combined with 10% FBS, provides a soil with relatively high salt and low protein content. An aliquot of a solution was deposited and dried on either a stainless steel surgical blade or small strip of polytetrafluoroethylene plastic. A simulated rinsing or cleaning process was then performed and the soil release rate was monitored via a chloride ion specific electrode for sodium chloride (NaCl) or a spectrophotometric technique based upon the o-phthalic dialdehyde (OPA) assay for total protein. The specific conditions and results for these experiments follow.

In the first experiment, 100 microliters of sodium chloride solution was inoculated on each SS blade. Eight blades were utilized for the experiment. Each blade was dried for 70 minutes in the oven at 35° C., followed by 30 minutes at room temperature. Eight glass vials were used for soaking the blades, one for each blade. Each vial contained 20 ml of deionizeded water. Soak times ranged from 0–60 seconds. The amount of sodium chloride released into the deionizeded water was monitored with a chloride ion selective electrode. FIG. 1 illustrates the results of the experiment. FIG. 1 is a graph of the sodium chloride release rate of sodium chloride inoculated stainless steel blades in deionizeded water at room temperature.

Figure 2:
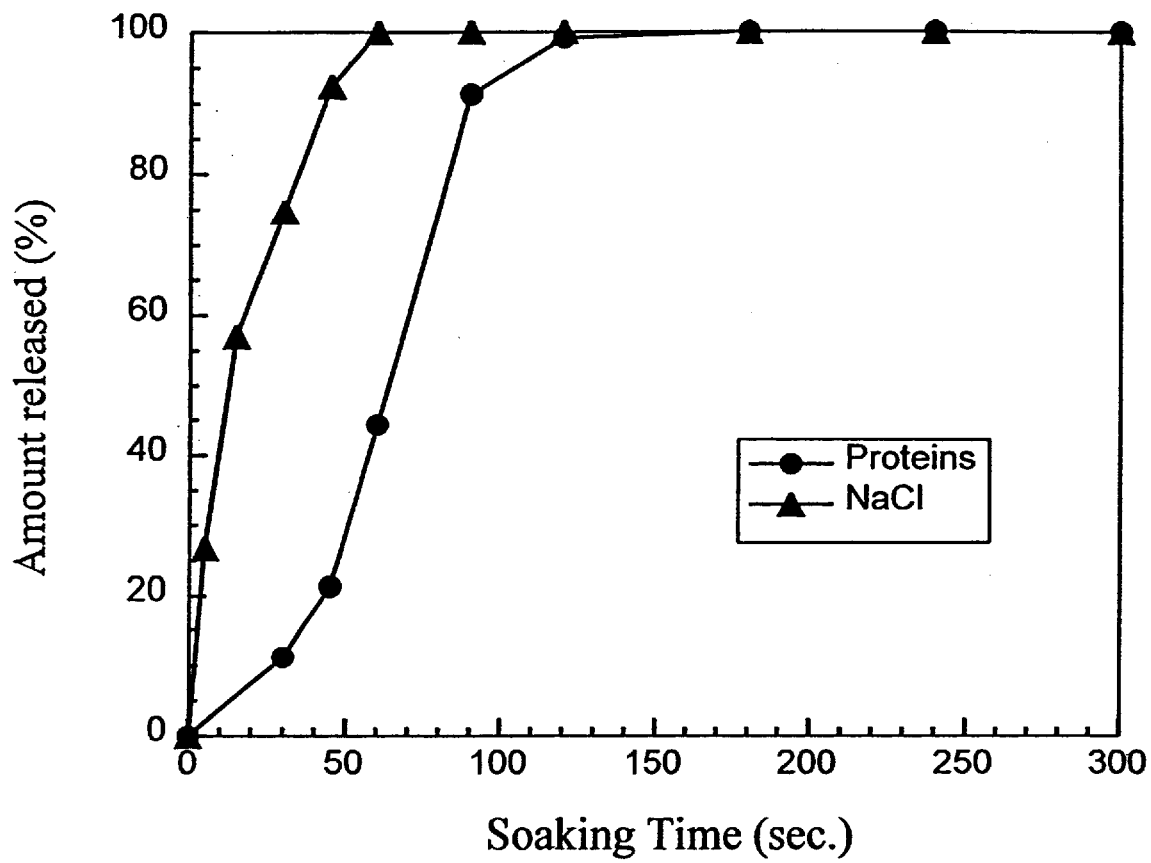
FIG. 2 is a graph of the albumin and sodium chloride release rates of albumin-solution inoculated stainless steel blades in deionized water at room temperature.

In the second experiment, 100 microliters of albumin solution was inoculated on each of eight SS blades. Each blade was dried for 70 minutes in the oven at 35° C., followed by an additional 30 minutes at room temperature. Eight glass vials were utilized to soak the blades, one for each blade. Each vial contained 20 ml of deionizeded water. Blades were soaked for between 0–300 seconds and the amount of protein and sodium chloride released into the deionizeded water from each of the blades was monitored with the appropriate technology described above. FIG. 2 is a graph of the albumin and sodium chloride release rates of albumin-solution inoculated stainless steel blades in deionizeded water at room temperature.

Figure 3:
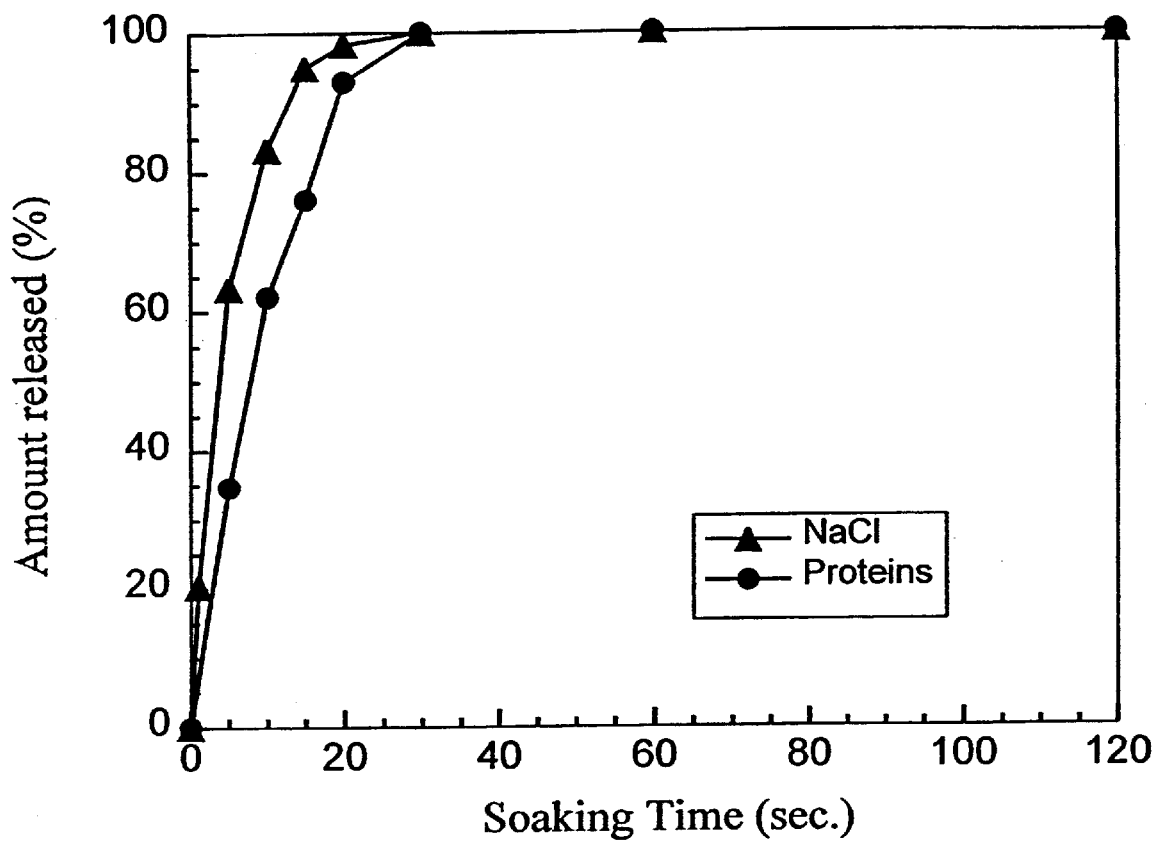
FIG. 3 is a graph of the sodium chloride and protein release rates of RPMI tissue culture medium+10% fetal bovine serum (FBS) contaminated stainless steel blades in deionized water at room temperature.

In the third experiment, 100 microliters of RPMI tissue culture medium with 10% FBS was inoculated on each of eight SS blades. Each blade was dried for 70 minutes in the oven at 35° C., followed by an additional 30 minutes at room temperature. Eight glass vials were used for soaking the blades, one for each blade. Each vial contained 20 ml of deionizeded water. The sodium chloride and protein release rates into the deionizeded water from the blades was monitored with the appropriate technology described above. FIG. 3 is a graph of the sodium chloride and protein release rates of RPMI tissue culture medium+10% FBS contaminated stainless steel blades in deionizeded water at room temperature.

Figure 4:
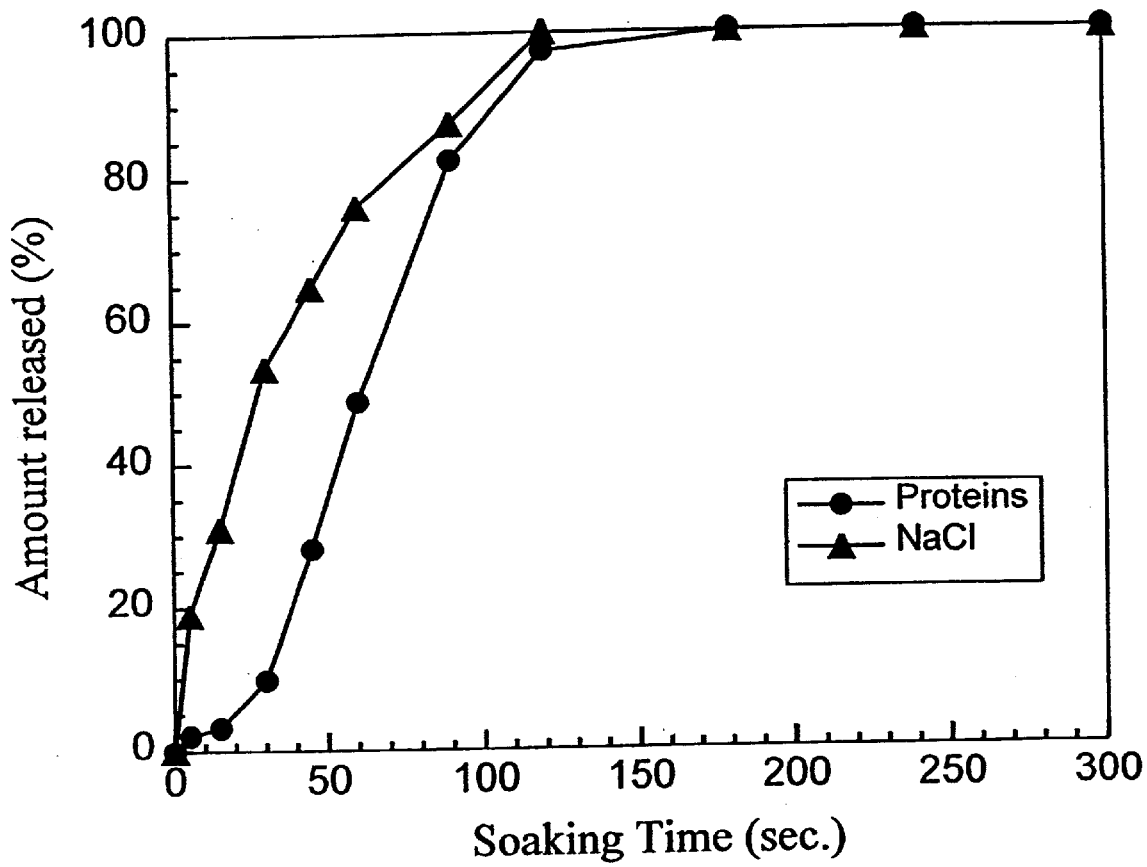
FIG. 4 is a graph of the sodium chloride and protein release rate of fetal bovine serum inoculated stainless steel blades in deionizded water at room temperature.

In the fourth experiment, 100 microliters of fetal bovine serum was inoculated on each of eight SS blades. Each blade was dried for 70 minutes in the oven at 35° C., followed by an additional 30 minutes at room temperature. Eight glass vials were used for soaking the blades, one for each blade. Each vial contained 20 ml of deionizeded water. Sodium chloride and protein release rates into the deionizeded water from the blade were monitored with the appropriate technology described above. FIG. 4 is a graph of the protein and sodium chloride release rates of fetal bovine serum inoculated stainless steel blades in deionizeded water at room temperature.

The results of the first four release experiments indicate that in all cases, the sodium chloride soil was removed from the SS blades prior to the protein-containing soil. Additionally, in all cases, the amount of time required to remove the protein-containing soil was not more than two times the time required to remove sodium chloride. Also, in all cases, a simple soak in 20 ml of deionizeded water cleaned all the blades in less than five minutes.

The next series of experiments explored the relationships between cleaning rates, cleaning solution composition, cleaning conditions and type of surface. In experiments 5–8, the blood solution used was the fresh recalcified bovine blood, which was prepared by gently mixing 20 parts of citrated bovine whole blood with 1 part of 0.5 molar calcium chloride solution at room temperature.

Figure 5:
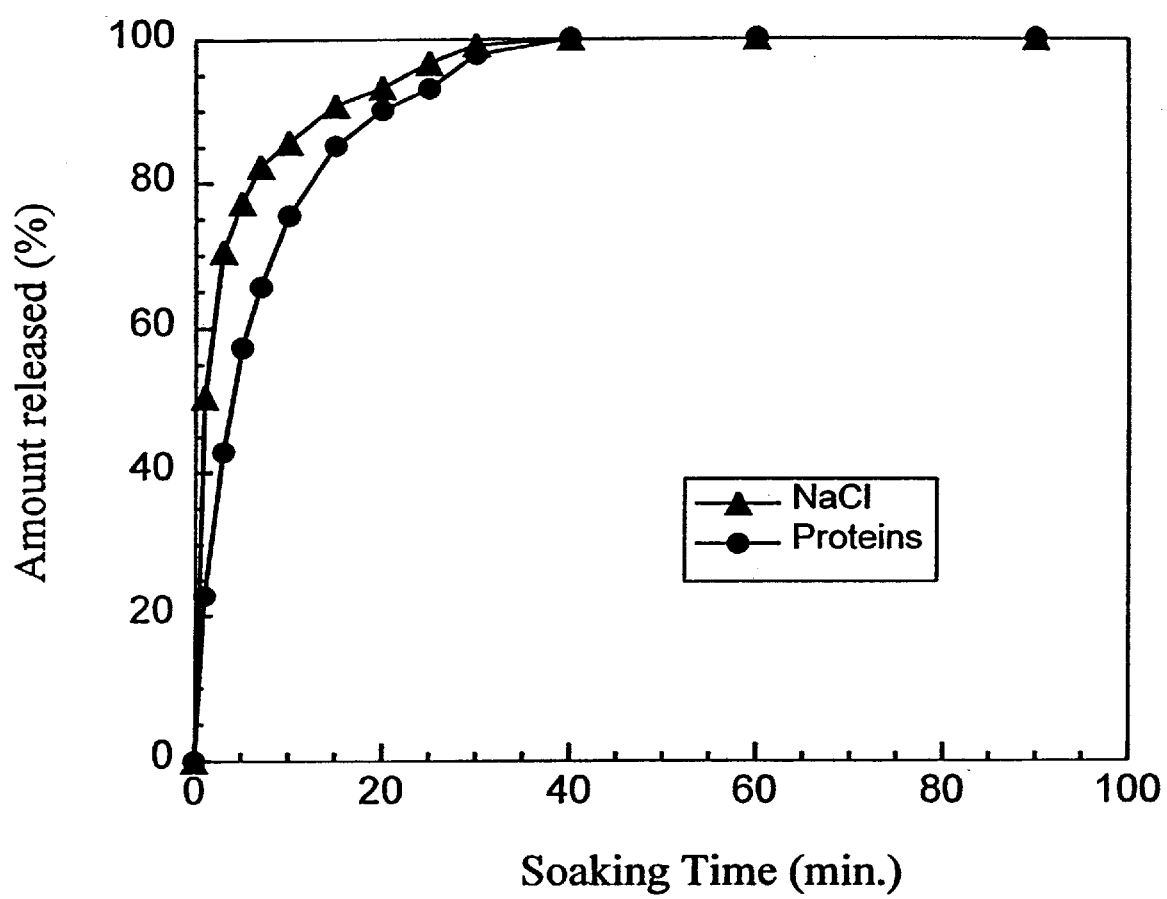
FIG. 5 is a graph of the sodium chloride and protein release rates of bovine whole blood inoculated stainless steel blades in 1% sodium dodecylsulfate solution at 23° C. and an agitation speed of 200 RPM.

In the fifth experiment, the release rate of blood from a set of blades was measured. Each set of blades container 12 SS surgical blades (Bard Parker, size #10). Five drops of blood solution were deposited on each blade. Each drop was 10 microliters. Blades were dried as in previous experiments. When starting the release rate measurement, the blades were placed at the bottom of a glass beaker (150 ml capacity) with the soaking solution in it. The soaking solution comprised 100 ml of 1% SDS (sodium dodecyl sulfate) solution and 0.2 ml of 5 M NaNO$_3$ at 23° C., with an agitation speed of 200 RPM. The agitation was generated by using a small Teflon stirring paddle (blade size=½"×½", 1/16" wide) which rotated at a constant speed by a mixer. Sodium chloride and protein release rates from the blades were monitored with the appropriate technology described above. FIG. 5 is a graph of the sodium chloride and protein release rates of the blood solution inoculated stainless steel blades in 1% SDS solution at 23° C. and an agitation speed of 200 RPM.

Figure 6:
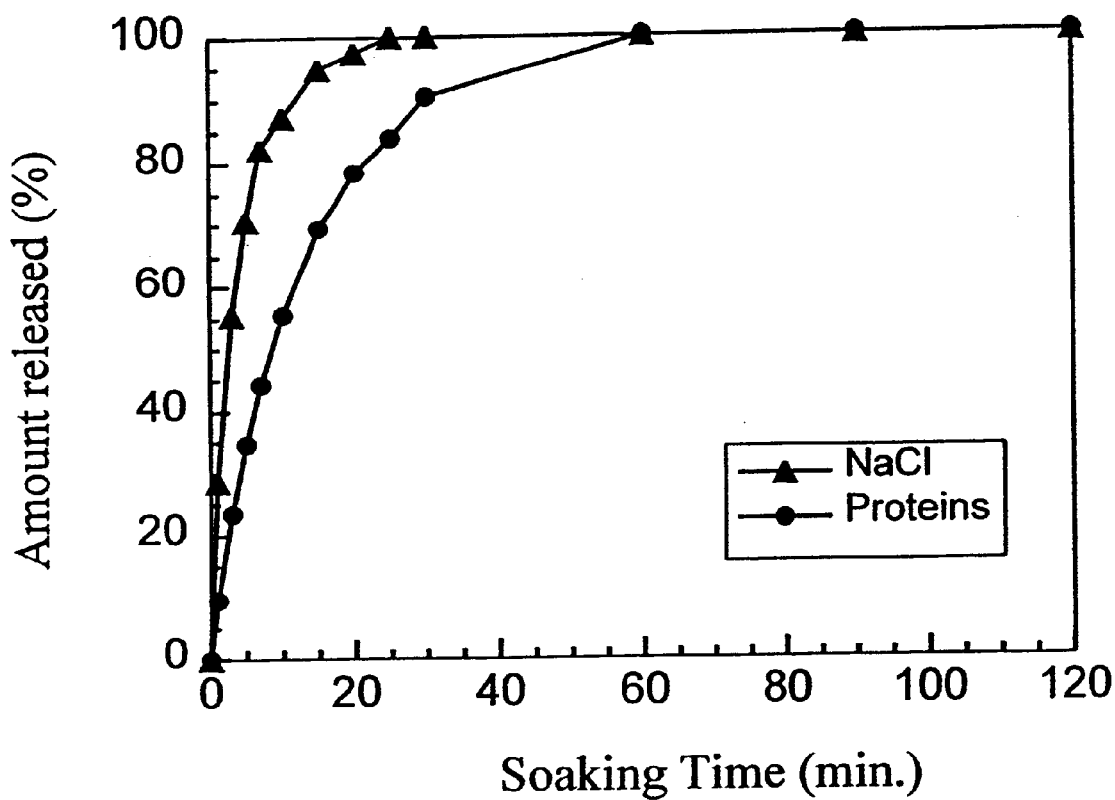
FIG. 6 is a graph of the sodium chloride and protein release rates of bovine whole blood inoculated polytetrafluoroethylene strips in 1% sodium dodecylsulfate solution at 23° C. and an agitation speed of 200 RPM.

In the sixth experiment, the release rate of blood from twelve PTFE strips was measured. Five drops of blood solution were deposited on each strip (35 mm×6 mm×2 mm). Each drop was 10 microliters. Strips were dried as in previous experiments. When starting the release rate measurement, the strips were placed at the bottom of a glass beaker (150 ml capacity) with soaking solution in it. The soaking solution comprised 100 ml of 1% SDS solution and 0.2 ml of 5 M NaNO$_3$ at 23° C., with an agitation speed of 200 RPM. Sodium chloride and protein release rates from the PTFE strips were evaluated with the appropriate technology described above. FIG. 6 is a graph of the sodium chloride and protein release rates of the blood solution inoculated PTFE strips in 1% SDS solution at 23° C. and an agitation speed of 200 RPM.

The results of the above two experiments once again show that the sodium chloride soil is released more readily than the protein soil. Moreover, the time required to remove the protein soil is not significantly longer than the amount of time required to remove the sodium chloride soil. Also, the whole blood deposit is more difficult to remove than the previous deposits, despite the use of a 1% SDS solution and agitation of the solution at 200 RPM. Also, there is some difference between the two surfaces, SS blades versus PTFE strips.

The next experiments explored the effects of cleaning solution agitation speed and temperature.

Figure 7:
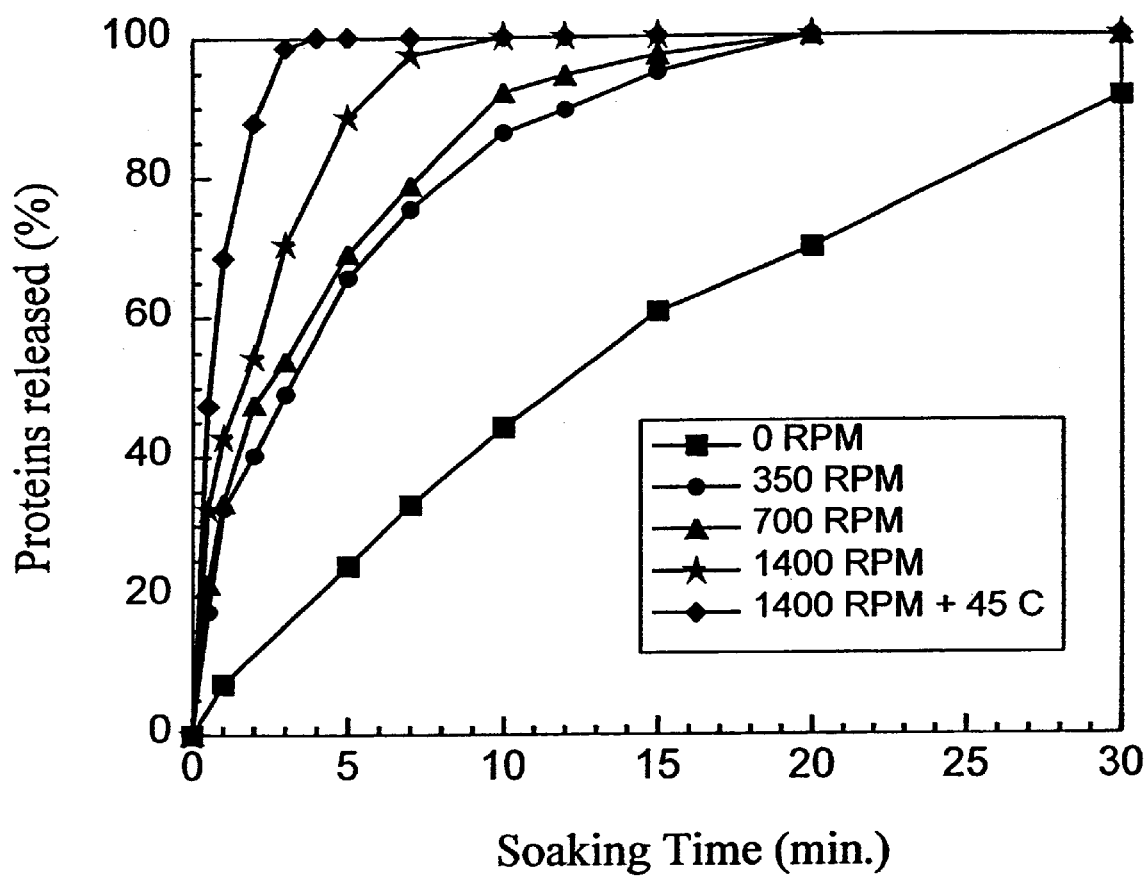
FIG. 7 is a graph of the protein release rates of bovine whole blood contaminated stainless steel blades in 1% sodium dodecylsulfate solution at 21° C., 45° C. and different agitation speeds.

In the seventh experiment, the release of blood from a set of blades at different agitation speed was measured. Each set of blades contained 12 SS surgical blades (size #10). Five drops of blood solution were deposited on each blade. Each drop was 10 microliters. Blades were dried as in previous experiments. When starting the experiment, one set of blades was placed in 100 ml of soaking solution at room temperature, and exposed to different agitation speeds (0, 350, 700, and 1400 RPM). Additionally, one set of blades was exposed to 1400 RPM at 45° C. The soaking solution comprised 100 ml of 1% SDS solution and 0.2 ml of 5 M NaNO$_3$. FIG. 7 is a graph of the protein release rates of the blood solution inoculated stainless steel blades in 1% SDS solution at 23° C. and 45° C. and different agitation speeds.

Figure 8:
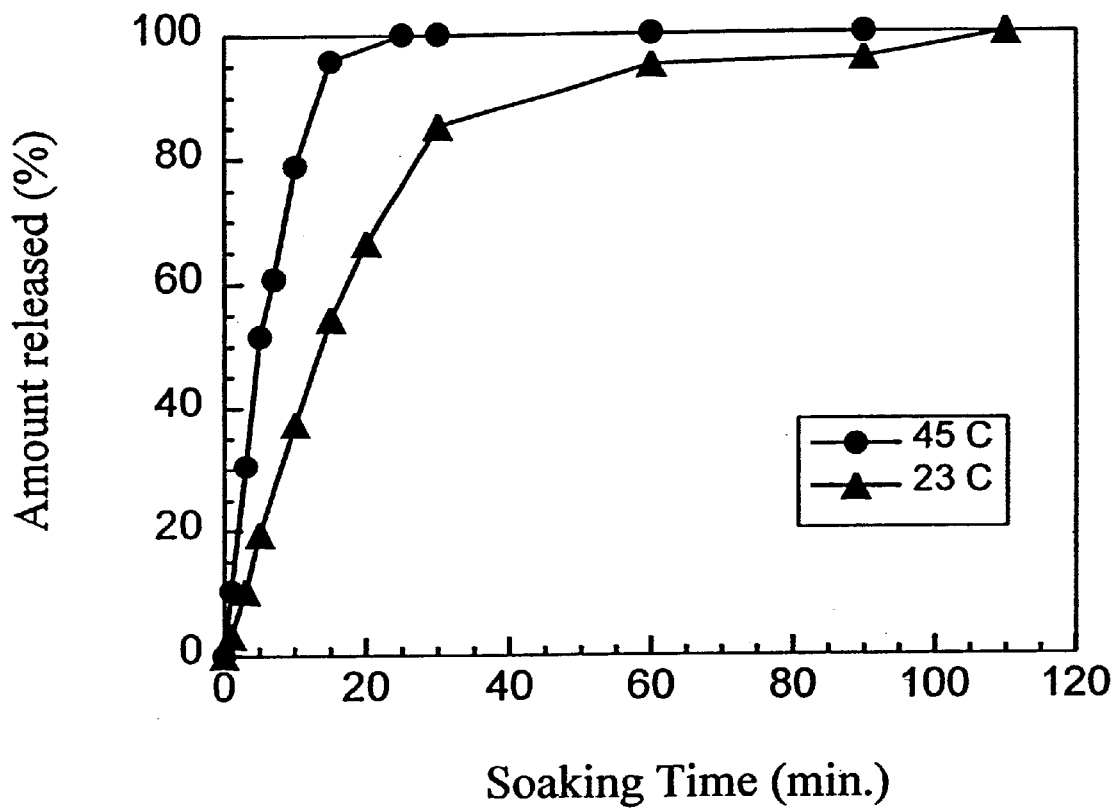
FIG. 8 is a graph of the protein release rates of bovine whole blood inoculated polytetrafluoroethylene strips in deionizeded water at different temperatures.

In the eighth experiment, the release rate of blood from a set of PTFE strips at two different temperatures was measured. Each set contained 12 PTFE strips. Five drops of blood solution were deposited on each strip. Each drop was 10 microliters. Strips were dried as in previous experiments. When starting the release rate measurement, the strips were placed at the bottom of a glass beaker (150 ml capacity) with 100 ml soaking solution in it. One set of strips was utilized for an experiment conducted at 45° C. and the other set was utilized for an experiment conducted at 23° C. No agitation was applied for both batches. Protein release rates from the PTFE strips were evaluated with the appropriate technology described above. FIG. 8 is a graph of the protein release rates of the blood solution inoculated PTFE strips in 1% SDS solution at 23° C. and 45° C.

The preceding two experiments show that increasing solution agitation speed or temperature will result in a shorter cleaning time or faster release rate.

In summary, it has been discovered from the results of the above release rate experiments that by correlating the release rate of various soils, one can monitor the release of a selected soil to ensure that adequate cleaning has taken place. In most situations, one can employ a cleaning time of not more than two to three times the amount of time required to remove the inorganic soil to be assured that adequate protein soil removal has occurred. Additionally, temperatures up to about 45° C. can be effectively employed to increase the cleaning rate. Also, agitation can be employed to increase cleaning effectiveness. Cleaning solution composition will affect cleaning rate, but in many cases, warm water (e.g. 30–50° C.) will adequately remove all soils.

One aspect of the present invention provides an apparatus for monitoring a cleaning process for a medical device. Preferably, the apparatus is capable of determining when the device is sufficiently cleaned so that the device can be sterilized. The apparatus comprises a soil detector, capable of detecting inorganic and/or organic soil on a medical device or in a liquid utilized in a cleaning or cleaning monitoring process or on a soil-covered standard which can serve as a surrogate indicator of cleanliness for the medical device.

Inorganic soils include electrolytes such as sodium chloride, potassium chloride, calcium chloride and other alkaline and alkaline earth salts, inorganic metal-containing compounds such as iron salts and all other inorganic compounds known to be present in the body and which may come in contact with a medical device which requires sterilization following use.

Organic soils include proteins, glycoproteins, lipoproteins, mucins, amino acids, polysaccharides, sugars, lipids, glycolipids and all other organic compounds known to be present in the body and which may come in contact with a medical device which requires sterilization following use. Organic soils also include whole, part, live, attenuated or dead microorganisms which may come in contact with a medical device. Microorganisms include all gram positive, gram negative, enteric and non-enteric microorganisms, yeasts, fungi and viruses.

The apparatus of the invention is suitable for monitoring a cleaning process for a wide variety of medical devices, including critical items that enter sterile tissues such as surgical instruments, semi-critical items that contact broken skin or mucous membranes such as endoscopes, arthroscopes, dental instruments and some anaesthetic equipment and non-critical items that contact intact skin.

Liquids utilized in cleaning processes include cleaning and rinsing liquids. A separate liquid utilized solely for the purpose of monitoring cleaning may also be employed and may thus be utilized in an apparatus comprising a soil detector. Cleaning processes include free-standing washing processes, integrated systems which include cleaning processes comprising a washing step followed by a sterilizing step and integrated systems which include cleaning processes in which cleaning and sterilization occur simultaneously.

The apparatus for monitoring cleaning can be integrated with a cleaning system for medical devices or a cleaning and sterilization system.

The soil detector of the apparatus of the invention may utilize a variety of detection technologies for monitoring cleaning, alone or in combination. Data obtained from one analyzer can be used to verify the reliability of data obtained from other analyzers. Soil detection technologies can be divided into two basic soil categories: (1) detection technologies suitable for detecting inorganic soils; and (2) detection technologies suitable for detecting organic soils. In many cases, however, a soil detection technology may be suitable for detecting both inorganic and organic soils.

The following are possible methods of detection. It should be understood that there are other suitable soil detection technologies not listed here. The following are illustrative of useful technologies which can be employed in the present invention.

A. Inorganic Soil (e.g. NaCl)
   1. Ion-Selective Electrodes
      1.1 Chloride Electrode Method
      Principle: A chloride electrode is composed of a glass body, reference solution, and a silver chloride/silver sulfide membrane. When the membrane is in contact with a chloride solution, an electrode potential develops across the membrane. This electrode potential is measured against a constant reference potential using a pH/mV/ion meter. The concentration of chloride ions, corresponding to the measured potential, is described by the Nernst equation:

$$E = E_o - S \log X$$

where:
E=measured electrode potential (mV)
Eo=reference potential (mV)
S=electrode slope
X=chloride ion concentration (M)

The detection range of common chloride electrodes is from 1M to $5.0 \times 10^{-5}$ M.

1.2 Sodium Electrode Method

Principle: A sodium electrode is composed of a glass body, reference solution, and a sensing membrane. The sensing membrane has a liquid internal filling solution in contact with a gelled organophilic membrane, which contains a sodium selective ion exchanger. When the membrane is in contact with a sodium solution, an electrode potential develops across the membrane. this electrode potential is measured against a constant reference potential with a pH/mV/ion meter. The concentration of sodium ions, corresponding to the measured potential, is described by the Nernst equation.

$$E = E_o - S \log X$$

where:
E=measured electrode potential (mV)
Eo=reference potential (mV)
S=electrode slope
X=sodium ion concentration (M)

The detection range of common sodium electrodes is from saturated to $1.0 \times 10^{-6}$ M.

When utilized as a soil detector, the electrode probe would be placed either directly inside the washing chamber in contact with a washing or rinsing liquid or inside a liquid conduit which is separate from the washing chamber and which is used for sampling a washing, rinsing or cleaning monitoring liquid. Additionally, more than one electrode probe may be utilized at the same time. In this latter case, one probe would be placed in continuous or intermittent or single contact with the fresh washing, rinsing or cleaning monitoring liquid. This probe would serve to provide the control potential reading for a soil-free liquid. A second probe would measure the potential of the wash, rinse or cleaning monitoring liquid which has been exposed to the soiled medical device. The potential readings of the two probes would be compared and the device could be considered sufficiently cleaned when the two potential readings are substantially equivalent or within a few percent (e.g., 3%) of one another.

2. Conductivity Method

Principle: Ions or electrolytes in solution can be determined and quantitated by measuring the electrical conductivities of electrolyte solutions. The conductivity of a solution depends on the number of ions present and the mobilities of the ions. Sodium chloride (NaCl) is a strong electrolyte and is completely ionized in solution. As a result of its complete ionization, the conductivity of a NaCl solution is proportional to the concentration of NaCl in the solution. Weak electrolytes, such as acetic acid, are not completely ionized in solution and thus have low conductance and large increases in conductance on dilution, where more ionization occurs. The molar conductivity (Λ) is defined as $$\Lambda = k/c$$

where:
c: the molar concentration of added electrolyte
k: the conductivity

The conductivity of a solution is generally measured with a probe containing two electrodes along with suitable electrical circuitry such as a Wheatstone Bridge for measuring the current between the electrodes. The conductivity of a solution is derived from the total numbers of ions in solution derived from all of the strong and weak electrolytes present.

When utilized as a soil detector, the conductivity probe would be placed either directly inside the washing chamber in contact with a washing or rinsing liquid or inside a liquid conduit which is separate from the washing chamber and which is used for sampling a washing, rinsing or cleaning monitoring liquid. Additionally, more than one conductivity probe may be utilized at the same time. In this latter case, one probe would be placed in continuous or intermittent or single contact with the fresh washing, rinsing or cleaning monitoring liquid. This probe would serve to provide the control conductivity reading for a soil-free liquid. A second probe would measure conductivity of the wash, rinse or cleaning monitoring liquid which has been exposed to the soiled medical device. Conductivity readings of the two probes would be compared and the device could be considered sufficiently cleaned when the two conductivity readings are substantially equivalent or within a few percent (e.g., 3%) of one another.

3. Spectrophotometer Method 3.1 Chloride Ions Reagent $$2Cl(-) + Hg(SCN)_2 \rightarrow HgCl_2 + 2SCN(-)$$

$$SCN(-) + Fe^{+3} \rightarrow Fe(SCN)^{++}$$

(Reddish Brown, 460 nm)

Principle: Chloride ions react with chloride reagent to form Fe(SCN)++ ions (reddish brown color) with a maximum absorbance at 460 nm. Preferably, an automatic colorimeter or photometric autotitrator is employed with spectrophotometric techniques based upon the generation of a colored species from the soil compound analyzed.

4. Ion Chromatography

Principle: Refers to the separation of substances by their differential migration on an ion-exchange column or on a sheet impregnated with an ion exchanger. Ions (anions or cations) are separated on the basis of ion-exchange reactions that are characteristic of each type of ion. The common detectors for ion chromatography are conductometric, UV and electrochemical detectors. Ion chromatography can detect dissolved chloride ions in water where concentrations range from a detection limit of 0.02 mg/L to 80 mg/L.

Preferably, an automatic ion chromatograph is employed when using ion chromatography for soil detection.

5. Capillary Electrophoresis

Principle: Electrophoresis is the movement of a charged species in an electric field. Capillary electrophoresis utilizes capillary tubes. A key advantage in the use of capillary tubes for electrophoresis is an enhanced heat dissipation that permits the use of high potentials for separation. The use of high-potential fields leads to extremely efficient separations with a dramatic decrease in analysis time.

6. High-Performance Liquid Chromatography (HPLC)

Principle: Refers to the separation of the components of a solution following different migration of the solutes in a liquid flowing through a column packed with specific solid particles. Among the separations possible are peptides (by reversed phase chromatography), proteins and enzymes (hydrophobic and size exclusion modes of chromatography), amino acids, and inorganic and organometallic compounds. There are several detectors that can be selected for a HPLC system. They are: UV-VIS absorption, IR absorption, fluorometry, refractive index, conductometric, electrochemical, and radioactivity detectors. According to the sample and stationary phase type, several separation columns can be selected. The common columns are affinity, gel-filtration, and ion-exchange columns.

(1) Affinity Media:
A successful affinity separation requires that a biospecific ligand is covalently attached to a chromatographic bed material, the matrix.

(2) Gel Filtration
The separation is based on differences in the size and/or shape of the analyte molecules, which governs the analytes' access to the pore volume inside the column packing particles.

(3) Ion-Exchange
This method involves solute interactions with charged groups of the packing material, followed by elution with an aqueous buffer of higher ionic strength or a change in pH.

7. Conclusion

Any of a number of different techniques can be used to monitor inorganic soil. One convenient product for electrolyte testing is the "MultiPLY" integrated multisensor available from Daile International of Newark, Del.

B. Organic Soil (e.g. Proteins)

1. Spectrophotometer (Vis to UV, Wave Length 190 nm–900 nm)

1.1 OPA Method

Proteins-NH$_2$+o-phthalic dialdehyde+Thiol→1-alkylthio-2-alkylisoindol (OPA) (Fluorescent, 340 nm)

Principle: The amino groups of proteins react with the aldehyde groups of OPA in the presence of a thiol component (N$_1$N-dimethyl-2-mercapto-ethylammonium-chloride) to form a fluorescent compound (1-alkylthio-2-alkylisoindol). The fluorescent compound has a maximum absorbance at 340 nm.

1.2 Albumin Reagent Method

Albumin +Bromcresol purple→Stable complex ($C_{21}H_{16}Br_2O_5S_9$ FW=540.24) (610 nm)

Principle: Bromcresol purple binds quantitatively with serum albumin forming a stable complex, which can be detected at 610 nm. The amount of the complex produced is linearly proportional to the albumin concentration in the solution.

1.3 Lowry Micro Method

Principle: Dilute biuret reagent reacts with peptide bonds to yield a purple-blue complex. The color of this complex can be further intensified by the addition of phenol reagent. The increase in absorbance, read at 550–750 nm, is used to determine the protein concentration in the sample.

1.4 Microprotein-PR™ Method

Principle: When the pyrogallol complex (in the Microprotein—PR reagent) binds amino groups of proteins, the absorbance of the reagent is shifted. The increase in absorbance at 600 nm is directly proportional to protein concentration in the sample.

2. Liquid Chromatography or High-Performance Liquid Chromatography (HPLC)

Principle: Same as in the measurement of inorganic species.

3. Cyclic Voltammetry

Principle: When materials (metals, polymers, etc.) are brought into contact with blood protein, a layer of protein (mostly fibrinogen) is formed at the interface within a few seconds. As a result of protein adsorption, addition of proteins into protein-free solution will change the behavior of the currently density—potential (I vs. V) of metal electrodes in a cyclic voltammetry measurement. For example, the I-V behavior of a high copper alloy (2% zinc) is modified by the addition of proteins (albumin, fibrinogen, etc) to a supporting phosphate-saline electrolyte.

4. Radioactivity

Principle: Proteins are labeled with a radioactive isotope such as Technicium 99 or Iodine 125 and the radioactivity of the solution is measured to determine the amount of protein present. For example, the protein fibrinogen is labeled with $^{125}I$ using a twofold molar excess of iodine monochloride. The biological properties of labeled fibrinogen are unaffected by this labeling method. The concentration of fibrinogen in a solution is directly proportional to the radioactivity (or intensity of gamma radiation) of a solution containing labeled fibrinogen.

5. Quartz Crystal Microbalance (QCM) Method

Principle: The quartz crystal microbalance is a mass-sensitive detector based on an oscillating quartz wafer. The response of the QCM is extremely sensitive to mass changes at the solid-solution interface. When gold coated quartz crystals are brought into contact with blood protein, a layer of protein is formed at the interface within a few seconds. This small mass change can be easily detected by the QCM. The increase of mass (or decrease of frequency of oscillation) on the quartz crystal is directly proportional to the protein concentration in a solution.

6. FTIR Spectroscopy(Transmission and ATR)

Fourier transform infra-red (FTIR) spectroscopy can be used to identify and quantitate proteins in mixtures, both in solutions as well as on surfaces. Transmission FTIR studies of aqueous protein solutions indicate the identity and amounts of proteins present. Attenuated total reflectance (ATR) FTIR studies of protein-deposited surfaces can determine the identity and amounts of proteins on surfaces.

7. Electrophoresis

Principle: Electrophoresis is the movement of a charged species in an electric field. In general, protein molecules pick up hydrogen ions in acid solution to become positively charged. By varying the pH of the electrophoretic medium, the velocity of a protein can be altered. If for a given protein the pI (pH at which the protein is electrically neutral) is smaller than the pH, its charge will be negative and movement will be towards the positive electrode. Protein components with pI>pH will be positively charged and move in the opposite direction.

8. Capillary Electrophoresis

Principle: Same as in the measurement of inorganic species.

Additional technologies for detecting both inorganic and organic soils include potentiometry, particularly potentiometric autotitrators, and technologies for detecting particles in solution or the clarity of a solution. The clarity of a solution can be measured with a turbidimeter, comprised of a turbidity sensor with a flow cell. Turbidimeters operate typically with a photocell and provide an electrical signal which is easily integrated with other systems, such as a cleaning control system. Alternatively, the clarity of a solution can be determined through a measurement of the color, reflectance, absorbance, transmittance etc. of the liquid. Laser systems utilizing optical fibers for transmission from the laser and to the detector from the sample can also be employed for evaluation of solution clarity or many other properties.

Preferably, the apparatus of the invention employs detection technology for detecting soils wherein the detection technology is suitable for detecting the presence of the soils in a liquid utilized in the cleaning process. Preferably, the liquid is selected from the group consisting of a cleaning and rinsing liquid used during the cleaning process.

The apparatus of the invention may also employ detection technology wherein the detection technology is suitable for detecting the presence of the soil on a surface of a medical device. Preferably, the detection technology which is suitable for detecting the presence of soil on a surface of a medical device operates without contacting the surface of the device. For example, utilizing fiber optic technology, combined with reflectance spectrophotometry, one can directly monitor surface cleaning. Alternatively, detection technology suitable for detecting the presence of soil on the surface of a medical device may operate via direct surface contact. In other words, a probe from the detection technology may physically contact the surface of the medical device and thereby sense the amount of soil present on the surface in order to determine and quantitate the state of cleanliness of the medical device. In most cases, the physical contact of the probe with the device is transient. A technology suitable for this particular application is attenuated total reflectance (ATR) spectroscopy. ATR methods employ crystals which transmit the sensing radiation directly to the surface of the sample to be monitored. The crystal physically contacts the surface of the sample. ATR spectroscopy can be utilized with ultraviolet (UV) absorption spectrophotometry as well as infra-red spectroscopy technologies. ATR-UV technologies employ sapphire crystals as sampling probes. Fourier transform infra-red spectroscopy can be employed with a suitable ATR crystal as well.

Alternatively, an indirect detection technology may also be employed. This approach employs the same physical-chemical detection technologies and methods previously mentioned for other approaches. However, the medical device itself is not monitored for the degree of cleaning. Rather, a soil-deposited standard is inserted in the apparatus and monitored in place of the medical device itself.

The soil detector may employ continuous sampling of a liquid or of a surface of a medical device or soil-covered standard or may employ periodic or single sampling of the aforementioned liquid or device or standard. Periodic sampling may be carried out in uniform or nonuniform (i.e., random) intervals. The number of intervals can be as few as one as in single sampling. A single sampling interval is viable under the situation wherein the cleaning process takes place over a sufficient period of time such that there is a high degree of assurance that sufficient cleaning has taken place such that the device can be sterilized thereafter. However, preferably two or more sampling intervals are utilized by the soil detector to assess the amount of cleaning which has taken place. More preferably, three or more sampling intervals are utilized. Even more preferably four or more sampling intervals are utilized by the detection technology.

The ion-selective electrode method is preferred for use in a soil detector due to its sensitivity and specificity for measuring relevant electrolytes such as sodium and chloride as well as the relatively compact probe, durability of the probe, ease of use, real time measurement capability and electrical basis of operation. Electrode potential measurements may be taken continuously or intermittently and can be easily integrated with a control system for a cleaning or cleaning and sterilization apparatus. A control system for controlling the cleaning process may also be a part of the present invention.

The conductivity method is also preferred for use in a soil detector for the same reasons given for the ion-selective electrode method.

Another aspect of the present invention provides a method for monitoring a cleaning process for a medical device, comprising the step of measuring the soil removed from a medical device with the apparatus of the invention comprising a soil detector.

Preferably, the method comprises the further step of determining when the device is sufficiently cleaned so that it can be sterilized.

Preferably, the device is selected from the group consisting of critical items that enter sterile tissues, semi-critical items that contact broken skin or mucous membranes and noncritical items that contact intact skin. More preferably, the critical items that enter sterile tissues are surgical instruments. More preferably, the semi-critical items that contact broken skin or mucous membranes include endoscopes, arthroscopes, dental instruments and anaesthetic equipment.

Preferably, the method of the invention employs an apparatus comprising a soil detector, wherein the soil detector utilizes detection technology capable of detecting inorganic and/or organic soil. The inorganic soil is selected from the group consisting of inorganic electrolytes, alkaline and alkaline earth salts, inorganic metal-containing compounds and other inorganic compounds present in the human body which may come in contact with a medical device. The organic soil is selected from the group consisting of proteins, glycoproteins, lipoproteins, mucous, amino acids, polysaccharides, sugars, lipids, glycolipids, other organic compounds present in the human body which may come in contact with a medical device, microorganisms and viruses.

The detection technology utilized in the method of the invention is selected from the group consisting of ion-selective electrodes, conductivity, spectrophotometry, ion chromatography, capillary electrophoresis, high performance liquid chromatography, liquid chromatography, radioactivity, gravimetry, infra-red spectroscopy, potentiometry and turbidimetry.

The cleaning process monitored in the method of the invention is selected from the group consisting of an independent cleaning process comprising one or more cleaning steps, a cleaning process comprising one or more cleaning steps followed by a sterilization step and a cleaning process in which cleaning and sterilization occur simultaneously.

The apparatus comprising the soil detector utilized in the method of the invention measures soil removed from the device by detecting soil on the device or in a liquid utilized in the cleaning process or a cleaning monitoring process or on a soil-covered standard which is an indicator of cleanliness for the device. Preferably, the liquid utilized in the cleaning process is a cleaning liquid.

The method of the invention wherein the liquid is a cleaning liquid and the detecting is of the soil in the liquid comprises the steps of:

(a) detecting the soil in the liquid prior to the cleaning process; and (b) detecting the soil in the liquid during or after the cleaning process.

The aforementioned method preferably further comprises the step of determining if the soil in step (b) is substantially equal to the soil in step (a), wherein if the soil detected in step (b) is substantially equal to the soil detected in step (a), the device is considered to be sufficiently cleaned so that it can be sterilized.

The amount of soil detected in one step may be considered to be substantially equal to the amount of soil detected in another step if the two values are within an acceptable range. In many instances, an acceptable range would be up to a 10% difference, more preferably within 3–5%.

If the soil determined in the aforementioned method in step (b) is not substantially equal to the soil determined in step (a), either the cleaning step or rinsing step or all steps of the cleaning process are repeated until the soil determined in step (b) is substantially equal to the soil determined in step (a).

Figure 9:
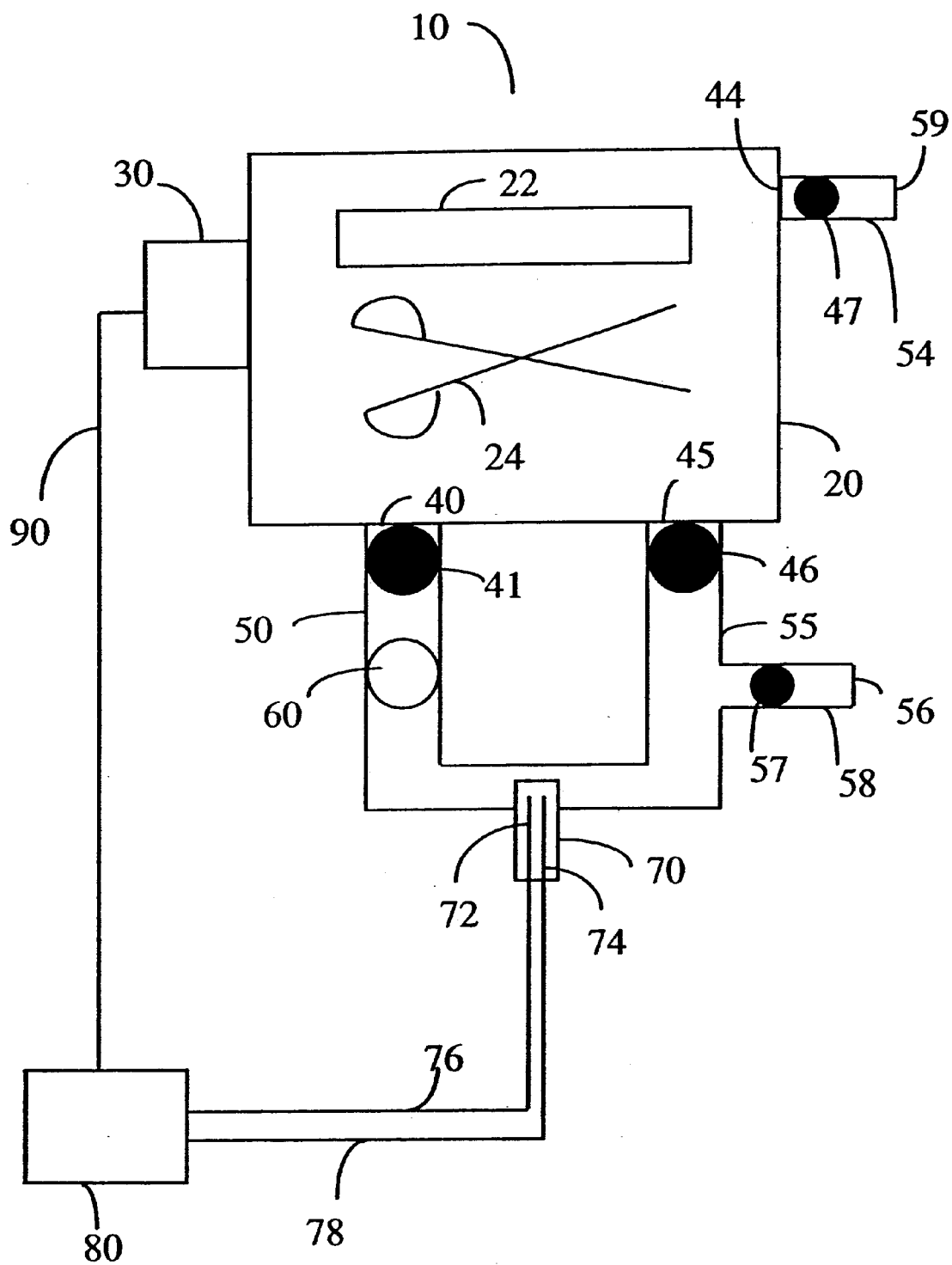
FIG. 9 is a schematic diagram of one embodiment of the apparatus of the invention in which the method of the invention can be practiced.

One embodiment of an apparatus for monitoring a cleaning process for a medical device or instrument comprising a ion-selective electrode-based soil detector is illustrated in FIG. 9. FIG. 9 illustrates an apparatus 10 which contains a washing chamber 20 for washing medical devices and instruments such as a medical device 22 with a lumen and surgical instrument 24. The washing chamber 20 may also be utilized for sterilization. Washing chamber 20 has a liquid outlet 40 with valve 41 and liquid inlet 45 with valve 46. Liquid outlet 40 and liquid inlet 45 are utilized to transport a washing or rinsing liquid out of washing chamber 20 and back into chamber 20. Liquid outlet 40 is connected through valve 41 to liquid conduit 50 which in turn is connected to liquid pump 60. Liquid conduit 50 transports a washing or rinsing liquid to pump 60 from the washing chamber 20. Pump 60 pumps the washing or rinsing liquid from washing chamber 20 through liquid outlet 40, valve 41 and liquid conduit 50 into liquid conduit 55. Liquid conduit 55 returns the liquid through valve 46 and liquid inlet 45 to the washing chamber 20. Liquid conduit 55 is also connected to liquid conduit 58 which contains a valve 57 and liquid inlet 56. Liquid inlet 56 is used for the inlet of any of the liquids utilized in the washing or rinsing process. Liquid inlet 56 allows, for example, the inlet of a fresh wash, rinse or cleaning monitoring liquid into conduit 55 so that a potential reading may be taken by electrode probe 70 which is positioned inside conduit 55. Washing chamber 20 also contains a liquid outlet 44 which is connected to valve 47. Valve 47 is connected to conduit 54 which in turn is connected to drain outlet 59. Liquid outlet 44 and the aforementioned connected parts are utilized for draining chamber 20 after a wash or rinse cycle.

The electrode probe 70 is utilized for soil detection within the washing or rinsing liquid. Electrode probe 70 contains a first electrode 72 and second electrode 74. Liquid flowing through conduit 55 passes by both the first electrode 72 and the second electrode 74. The ions in the liquid produce a current which is transmitted via electrical cable 76 and electrical cable 78 to the electrical circuitry 80 for the electrode detector. The electrical circuitry 80 is connected via an electrical connection 90 to the washing control system 30. The washing control system 30 is directly connected to the washing chamber 20 and controls all aspects of the washing process.

The method of the invention for monitoring a cleaning process for a medical device, utilizing the apparatus of the invention illustrated in FIG. 9, operates as follows: All valves are initially in the closed position. Valve 57 is opened and fresh, clean wash or rinse water is allowed to flow into inlet 56 from a wash or rinse water source (not shown). Electrode potential readings are taken initially by the electrode probe 70 of the clean wash or rinse liquid which does not contain any soil. Preferably, in this embodiment of the method, a potential reading is taken of the clean wash liquid. This represents the time 0 potential reading. Thereafter, valve 46 is opened allowing wash water to enter chamber 20, filling it to prepare for the wash cycle. Alternatively, valves 46 and 57 can be opened simultaneously, so that a time 0 reading may be taken during filling of the chamber 20. A time 0 reading may also be taken during the washing cycle, if desired. Valves 46 and 57 are then closed and the wash cycle is initiated. The wash cycle is run over a time period determined by the type of medical devices and instruments present. Generally, this time period is less than about one hour. Preferably, this time period is less than about 30 minutes. Even more preferably, this time is less than about 15 minutes. At the end of the wash cycle, valve 47 is opened and the dirty wash water is allowed to flow out of the chamber through outlet 59. Valve 47 is closed after the chamber is emptied. Valves 45 and 57 are once again opened, allowing fresh rinse water to enter chamber 20. After chamber 20 is filled, valves 45 and 57 are once again closed. A rinse cycle is then performed. This cycle generally is of a fraction of or is equal to the duration of the wash cycle. One or more potential readings are taken of the rinse liquid during or at the end of the rinse cycle. This is performed by simultaneously opening valves 41 and 46 and turning pump 60 on to pump the rinse liquid into conduits 50 and 55 until the rinse liquid contacting the electrode probe 70 is equivalent to the rinse liquid inside the chamber 20. If the potential of the rinse liquid following the wash cycle is substantially equal to the time 0 potential reading, adequate cleaning has been achieved. If not, either the rinse cycle or wash and rinse cycle are repeated until the potential reading of the rinse solution attains the desired value. At this stage, the medical device 22 and instrument 24 inside the chamber can be sterilized in the second step of a two step sequential cleaning and sterilization process.

Figure 10:
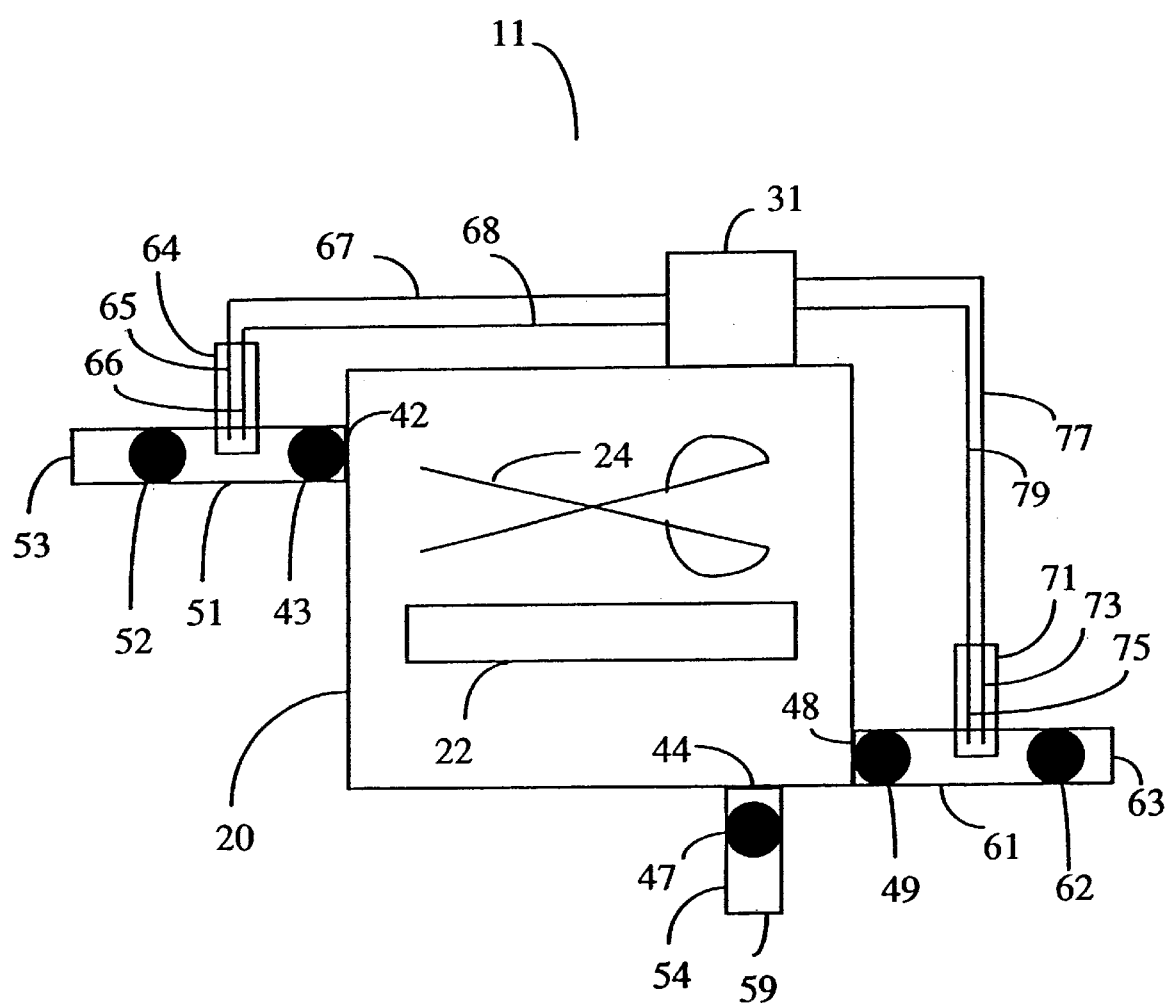
FIG. 10 is a schematic diagram of a second embodiment of the apparatus of the invention in which the method of the invention can be practiced.

Another embodiment of an apparatus for monitoring a cleaning process for a medical device or instrument comprising an ion-selective electrode-based soil detector is illustrated in FIG. 10. FIG. 10 illustrates an apparatus 11 which contains a washing chamber 20 for washing medical devices and instruments such as a medical device 22 with a lumen and surgical instrument 24. Washing chamber 20 can also be utilized for both cleaning and sterilization. The cleaning and the sterilization can take place simultaneously or sequentially. Preferably, the cleaning step is performed prior to the sterilization step inside chamber 20. Washing chamber 20 has a water inlet 53 which is connected to a water source (not shown) and also through valve 52 and conduit 51 to valve 43. Valve 43 is connected directly to inlet 42 leading directly to the inside of washing chamber 20. Washing chamber 20 also has water outlets 44 and 48. Water outlet 44 is connected to valve 47 and thereafter to conduit 54 which leads to the water drain outlet 59. The water drain outlet 59 is a dirty water outlet used primarily to purge the washing chamber 20 of dirty water. Water outlet 48 is connected to valve 49 and thereafter to conduit 61 which leads to valve 62. Valve 62 leads to the rinsing water outlet 63. Conduit 51 in the water inlet line contains a first electrode probe 64 with a first electrode 65 and a second electrode 66. The first electrode 65 is connected to electrical cable 67 and the second electrode 66 is connected to electrical cable 68. Electrical cables 67 and 68 lead from the electrode probe 64 to electrical circuitry 31 which comprises the ion-selective electrode electrical circuitry as well as the washing or washing and sterilization control circuitry. Similarly, a second electrode probe 71 is positioned in the rinsing water outlet conduit 61 between valves 49 and 62. Electrode probe 71 has a first electrode 73 and a second electrode 75. Electrodes 73 and 75 are connected to electrical cables 77 and 79, respectively. Electrical cables 77 and 79 are connected directly to electrical circuitry 31.

The method of the invention for monitoring a cleaning process for a medical device utilizing the apparatus of the invention illustrated in FIG. 10, operates as follows: valves 52 and 43 in the water inlet conduit 51 are opened and water is allowed to flow through water inlet 42 into the washing chamber 20 until chamber 20 is sufficiently filled for a cleaning cycle. This water is fresh, clean water with no soil. A potential reading is taken of this water with the electrode probe 64 and the electrical circuitry 31 stores this reading. Valves 52 and 43 are then closed. A first cleaning cycle is performed within the washing chamber 20. This cleaning cycle is generally less than about one hour. Preferably, the cleaning cycle is less than about 30 minutes. More preferably, the cleaning cycle is less than about 15 minutes. Valve 47 opens at the end of this first cleaning cycle. The dirty wash water is expelled from chamber 20 through an outlet 44 after valve 47 opens. Valve 47 is closed after all of the dirty wash water is expelled from the washing chamber 20. Thereafter, valves 53 and 43 are once again opened and clean, fresh rinse water is allowed to flow into the washing chamber 20 through the inlet port 42. A second potential reading of the clean, fresh rinse water coming into the chamber may be taken with the first electrode probe 64. Valves 52 and 43 are then closed and a rinsing cycle within chamber 20 is initiated. This rinsing cycle is generally less than about one hour. Preferably, the rinsing cycle is less than about 30 minutes. More preferably, the rinsing cycle is less than about 15 minutes. At the end of the rinse cycle, valves 49 and 62 in the rinsing water outlet line 61 are opened allowing the rinsing water to flow out of the washing chamber 20 past the second electrode probe 71. A potential reading is taken by electrode probe 71 and transmitted to electrical circuitry 31. A comparison is made by electrical circuitry 31 of the potential of the rinsing water taken by electrode probe 71 and the potential of the fresh, clean rinsing water taken by electrode probe 64. If these two values are substantially equivalent, meaning that they are identical or within a few percent of one another, then no further washing and rinsing is required. Valves 49 and 63 are closed once all of the rinse liquid has been expelled from chamber 20. However, if the two readings are not substantially equal in absolute value, then additional rinsing is initiated and performed as before. The second rinse cycle may be either a fraction of the duration of the first rinse cycle or may be equivalent in duration to the first rinse cycle. Potential readings are taken as before during the first rinse cycle and the potential reading of the rinse liquid after it has contacted the medical devices and instruments is compared once again to the potential reading of the fresh clean rinse liquid. Once these two readings are substantially equivalent, then adequate cleaning has taken place and no further washing and rinsing is required. At this stage, the medical device 22 and instrument 24 inside the chamber can be sterilized in the second step of a two step sequential cleaning and sterilization process. The chamber 20 may then be opened via a door (not shown) and device 22 and instrument 24 removed for use.

Figure 11:
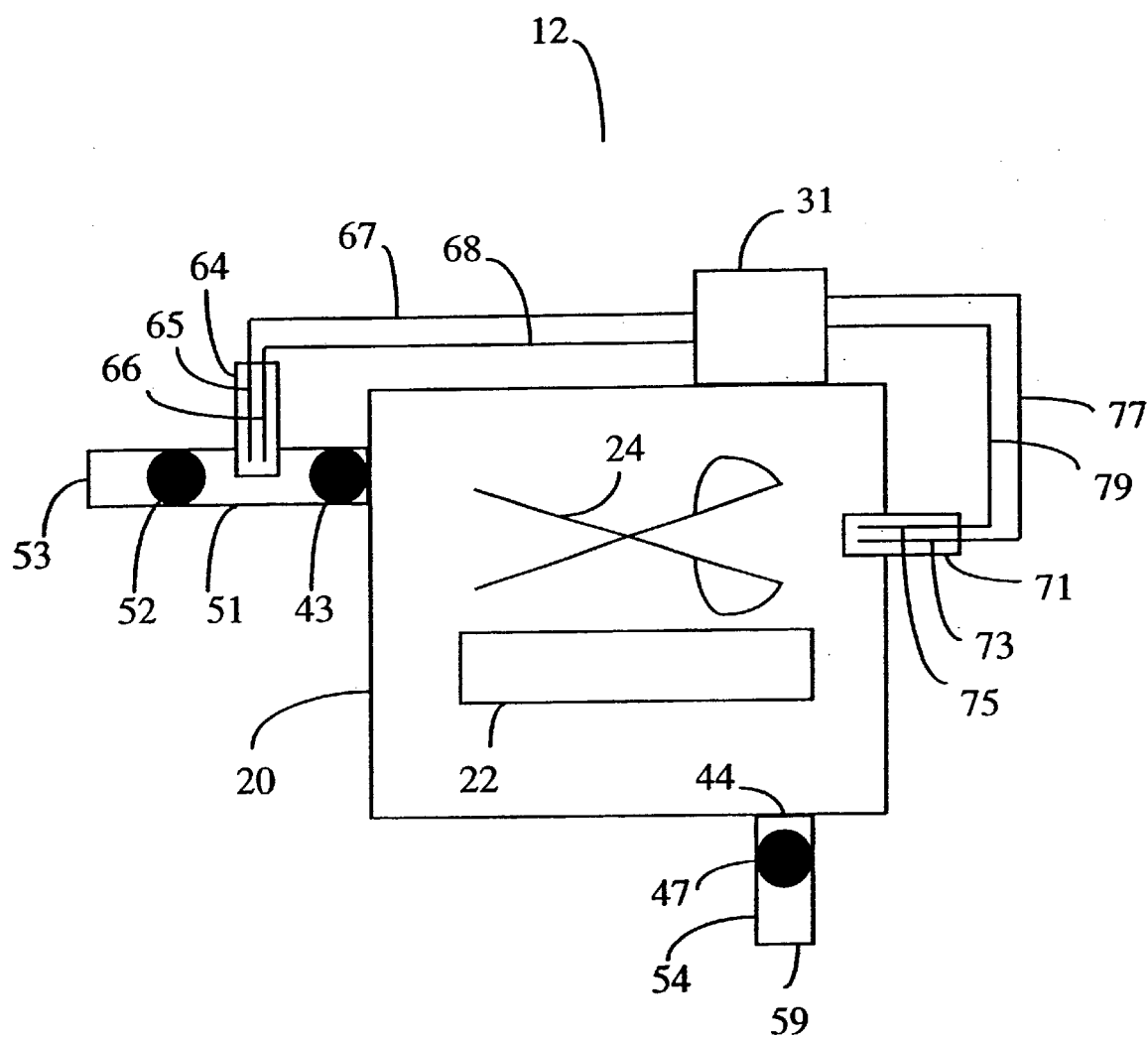
FIG. 11 is a schematic diagram of a third embodiment of the apparatus of the invention in which the method of the invention can be practiced.

Another embodiment of the apparatus for monitoring a cleaning process for medical devices or instruments comprising an ion-selective electrode-based soil detector is illustrated in FIG. 11. FIG. 11 illustrates an apparatus 12 which contains a chamber 20 for washing medical devices and instruments such as a medical device 22 with a lumen and surgical instrument 24. Washing chamber 20 may also be utilized for sterilization. The sterilization may occur simultaneously with cleaning or may take place following the cleaning step. Apparatus 12 contains all of the components of apparatus 11 illustrated in FIG. 10, with the exception of outlet 48, valve 49, valve 62, conduit 61 and rinsing water outlet 63. Apparatus 12 operates in much the same manner as apparatus 11 illustrated in FIG. 10. In the case of apparatus 12 illustrated in FIG. 11, however, all of the washing and rinsing liquid exits washing chamber 20 through the outlet 44. Otherwise, all of the steps of the method of the invention for monitoring the cleaning process described previously and which are utilized for apparatus 11 as illustrated FIG. 10 apply to apparatus 12 illustrated in FIG. 11. Once again, the second electrode probe 71 will take potential readings of the rinsing liquid after it has contacted the medical device and instrument 24 during or at the end of a rinse cycle following a wash cycle. In this particular embodiment, however, these readings are taken inside the washing chamber 20, rather than inside conduit 61 as in apparatus 11 illustrated in FIG. 10. The principal advantage of apparatus 11 as illustrated in FIG. 10, is with the placement of the second electrode probe 71 inside conduit 61. The placement of the second electrode probe 71 inside conduit 61 allows for the complete protection of the second electrode probe 71 from becoming over-contaminated by soils. This ensures that the electrode probe 71 will repeatedly perform the potential readings accurately and precisely. In some instances, however, it is not necessary to place the second electrode probe 71 inside a separate conduit 61. Thus, the apparatus 12 illustrated in FIG. 11 is useful for some washing applications, particularly wherein it is known that soil contamination of the electrode probe 71 is not a problem.

The apparatus illustrated in FIGS. 10 and 11 can be further modified, for example, to include a detector which detects inorganic soil and a detector which detects organic soil. The apparatus can have a second chamber in controllable fluid communication with the chamber 20, and the detectors can be placed in the second chamber. A soiled standard can also be provided, for example, in the second chamber, and the cleaning condition and the soil coverage on the soiled standard are so determined that the degree of cleanness of the standard serves as an indication of the completeness of the cleaning of the device to be cleaned.

Figure 12:
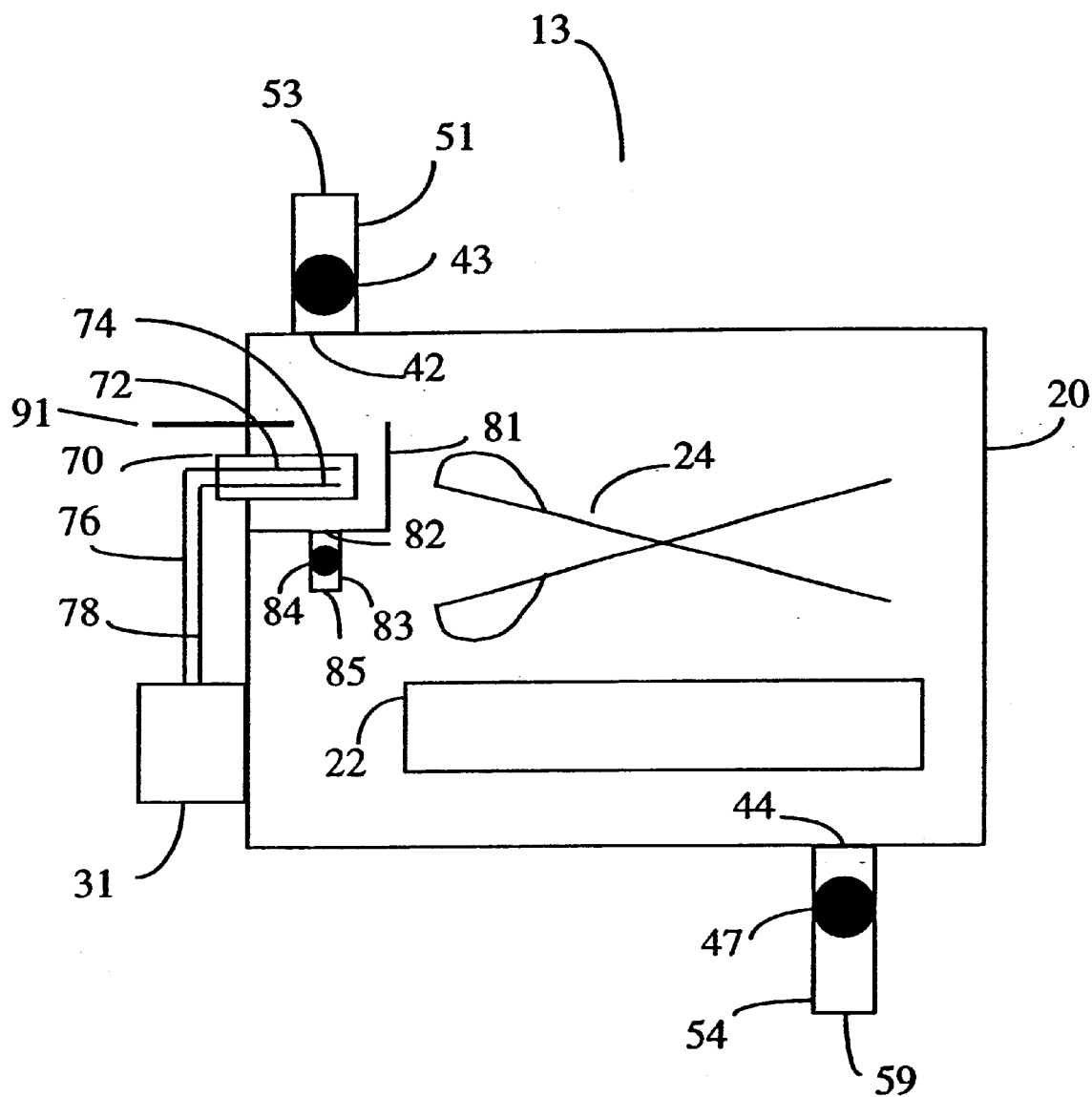
FIG. 12 is a schematic diagram of a fourth embodiment of the apparatus of the invention in which the method of the invention can be practiced.

FIG. 12 illustrates another embodiment of an apparatus for monitoring a cleaning process for a medical device or instrument comprising an ion-selective electrode-based soil detector. FIG. 12 illustrates an apparatus 13 which contains a washing chamber 20 for washing medical devices and instruments such as a medical device 22 with a lumen and surgical instrument 24. As with other embodiments, washing chamber 20 can also be utilized for sterilization. Washing chamber 20 has a water inlet 42 which is connected through valve 43 to a water inlet conduit 51. The water inlet conduit 51 is connected to the water inlet 53. Water inlet 53 is connected to a water source (not shown). Washing chamber 20 also has components 44, 47, 54 and 59 which have the same placement, connections and water drain functions as seen in FIGS. 10 and 11. This embodiment of the apparatus of the invention illustrated in FIG. 12 has a single electrode probe 70 with a first electrode 72 and a second electrode 74. Electrodes 72 and 74 are connected to electrical cables 76 and 78, respectively. Electrical cables 76 and 78 are connected directly to electrical circuitry 31. Electrical circuitry 31 performs the same function as described with the apparatus of the invention illustrated in FIGS. 10 and 11. Electrode probe 70 is positioned inside a small water reservoir 81 which is positioned directly underneath the water inlet 42. Water reservoir 81 is designed to catch the first small volume of water which is let into washing chamber 20. This allows a potential reading to be taken of the fresh clean wash water prior to its contact with the medical device 22 and instrument 24. Reservoir 81 has a reservoir outlet and inlet 82 which is connected to reservoir outlet and inlet conduit 83. Reservoir outlet and inlet conduit 83 contains a reservoir outlet and inlet valve 84 and reservoir drain outlet and inlet 85.

The method of the invention for monitoring a cleaning process for a medical device, utilizing the apparatus that the invention illustrated in FIG. 12 operates as follows: Valve 43 is opened and fresh clean water, or other washing or rinsing liquid, is allowed to flow into washing chamber 20 through the inlet 42. The water reservoir 81 fills up allowing a potential reading to be taken of the fresh clean water by the electrode probe 70. This potential reading is stored in electrical circuitry 31 as the control potential reading. Water continues to flow inside washing chamber 20 through inlet 42 and fills reservoir 81. Reservoir valve 84 is opened. Water then flows from the reservoir 81 through reservoir conduit 83 and reservoir drain outlet and inlet 85 into washing chamber 20. Washing chamber 20 is filled sufficiently with the washing water so that a washing cycle may begin. Reservoir valve 84 is closed and the washing cycle is initiated as described in the method of the invention utilizing the apparatus of the invention illustrated in FIGS. 10 and 11. Prior to the initiation of the washing cycle, valves 43 and 47 are closed so that no liquid may flow into or drain from the washing chamber 20.

At this point, the electrode probe 70 can be isolated, totally or partially, from the dirty washing liquid in chamber 20. This can be achieved by numerous ways. For example, reservoir 81 is filled with fresh washing liquid and the electrode probe 70 is immersed in the fresh washing liquid while the cleaning is conducted in the chamber 20, so that the electrode probe is protected from the contamination caused by the dirty washing liquid. In another example, the electrode probe 70 can be moved into and out of contact with the liquid. Alternatively, reservoir 81 can be covered with a movable cap 91 during the cleaning process. An enclosure or a second chamber can be provided, which is made in controllable fluid communication with chamber 20, and a detector can be placed in the enclosure. Thus, during a cleaning process the fluid communication between the chamber 20 and the enclosure is cut off, for example, with a valve, and when measuring the soil concentration in the washing liquid the fluid communication is reestablished.

At the end of the washing cycle, the dirty wash water is allowed to flow out of washing chamber 20 through outlet 44 and drain outlet 59 through valve 47 which is opened for that purpose. Valve 47 is then closed and fresh rinse liquid is allowed to flow inside washing chamber 20 through inlet 53 and inlet 42 through valve 43 which is opened for that purpose. Once again, the rinse liquid flows into the reservoir 81, filling it and thereafter filling chamber 20 for the rinse cycle in the same process as previously described. Valve 43 is closed and a rinsing cycle takes place as previously described in the method of the invention utilizing the apparatus of the invention illustrated in FIGS. 10 and 11. Valve 84 is opened and rinse liquid is allowed to flow into reservoir 81. Alternatively, the level of the rinse liquid inside chamber 20 may be higher than the top of the sides of reservoir 81, allowing rinse liquid to fill reservoir 81. In this manner, an accurate potential reading can be taken of the rinsing liquid inside the reservoir 81 such that it is representative of the rinsing liquid inside the washing chamber 20. This second potential reading is compared to the potential reading taken of the fresh clean rinse liquid. The comparison in potential readings is done exactly as described before herein and a determination is made if sufficient rinsing and/or cleaning has taken place and an additional rinse or wash and rinse cycle are necessary.

Figure 13:
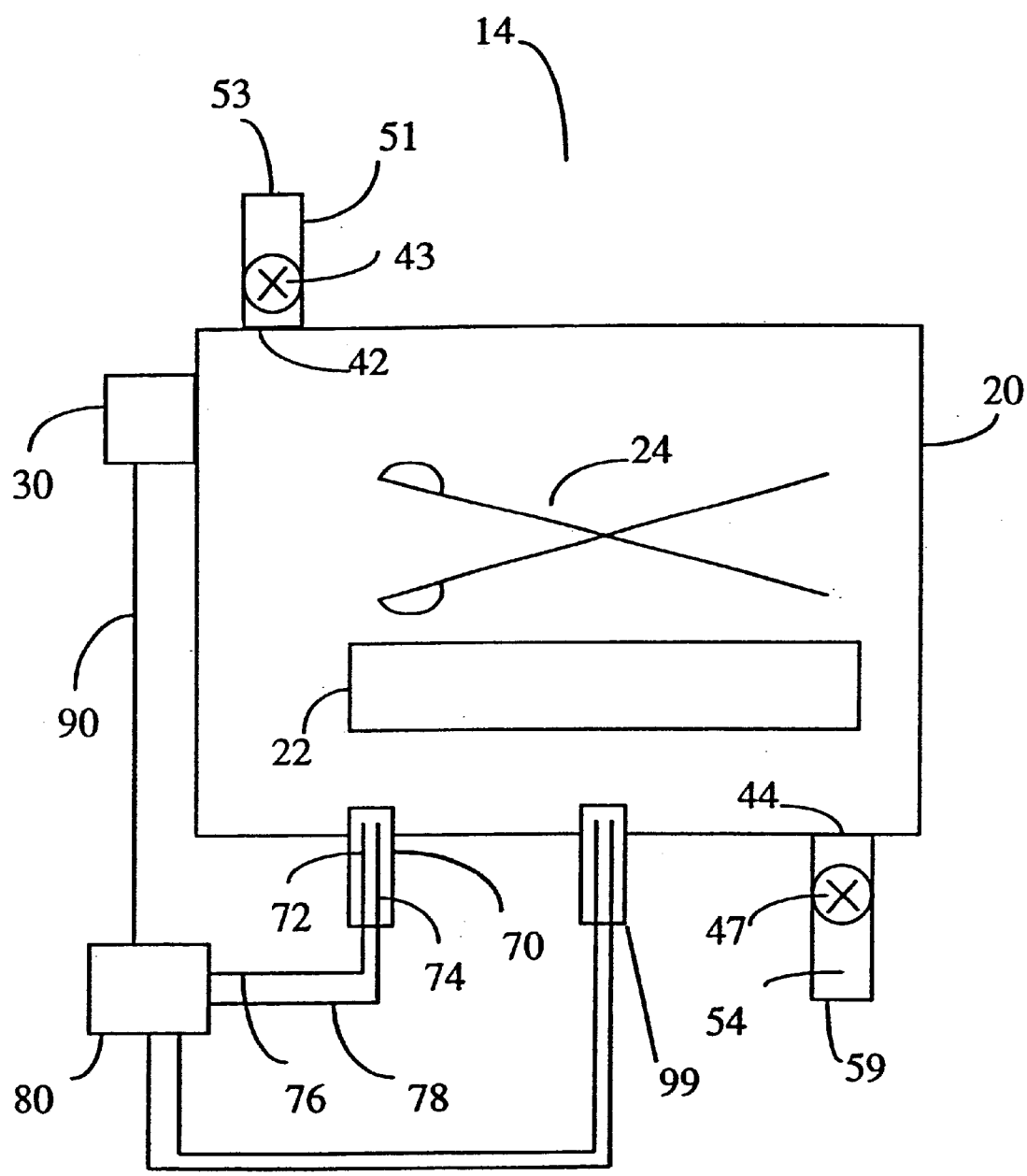
FIG. 13 is a schematic diagram of a fifth embodiment of the apparatus of the invention in which the method of the invention can be practiced.

FIG. 13 illustrates another embodiment of an apparatus for monitoring a cleaning process for a medical device or instrument comprising an ion-selective electrode-based soil detector. FIG. 13 illustrates an apparatus 14 which once again contains a washing chamber 20 for washing or washing and sterilizing medical devices and instruments as previously described. All components of apparatus 14 illustrated in FIG. 13 are the same as described with identically-numbered components in apparatus 13 illustrated in FIG. 12, with the exception of components 30,80 and 90.

Components 30, 80 and 90 are the same and have the same connections and functions as components 30, 80 and 90 illustrated in FIG. 9. Component 30 is the washing control system. Component 80 is the electrical circuitry for the electrode detector. Electrical circuitry 80 is connected via an electrical connection 90 to the washing control system 30. Component 31 illustrated in FIG. 12 performs the same function as components 30, 80 and 90 illustrated in FIGS. 9 and 13.

Reservoir 81, reservoir outlet and inlet 82, reservoir outlet and inlet valve 84, reservoir outlet and inlet conduit 83 and reservoir drain outlet and inlet 85 illustrated in FIG. 12 are also not utilized in apparatus 14 illustrated in FIG. 13. Apparatus 14 carries out the method of the invention in the same manner as apparatus 13 in FIG. 12, with the exception that reservoir 81 and associated outlet and inlet components 82–85 are not employed to hold a small volume of wash or rinse liquid to take a potential reading and subsequently release it. All potential readings are directly taken of the liquid inside chamber 20 instead. A second probe 99 or more probes can also be used to monitor additional soils.

Figure 14:
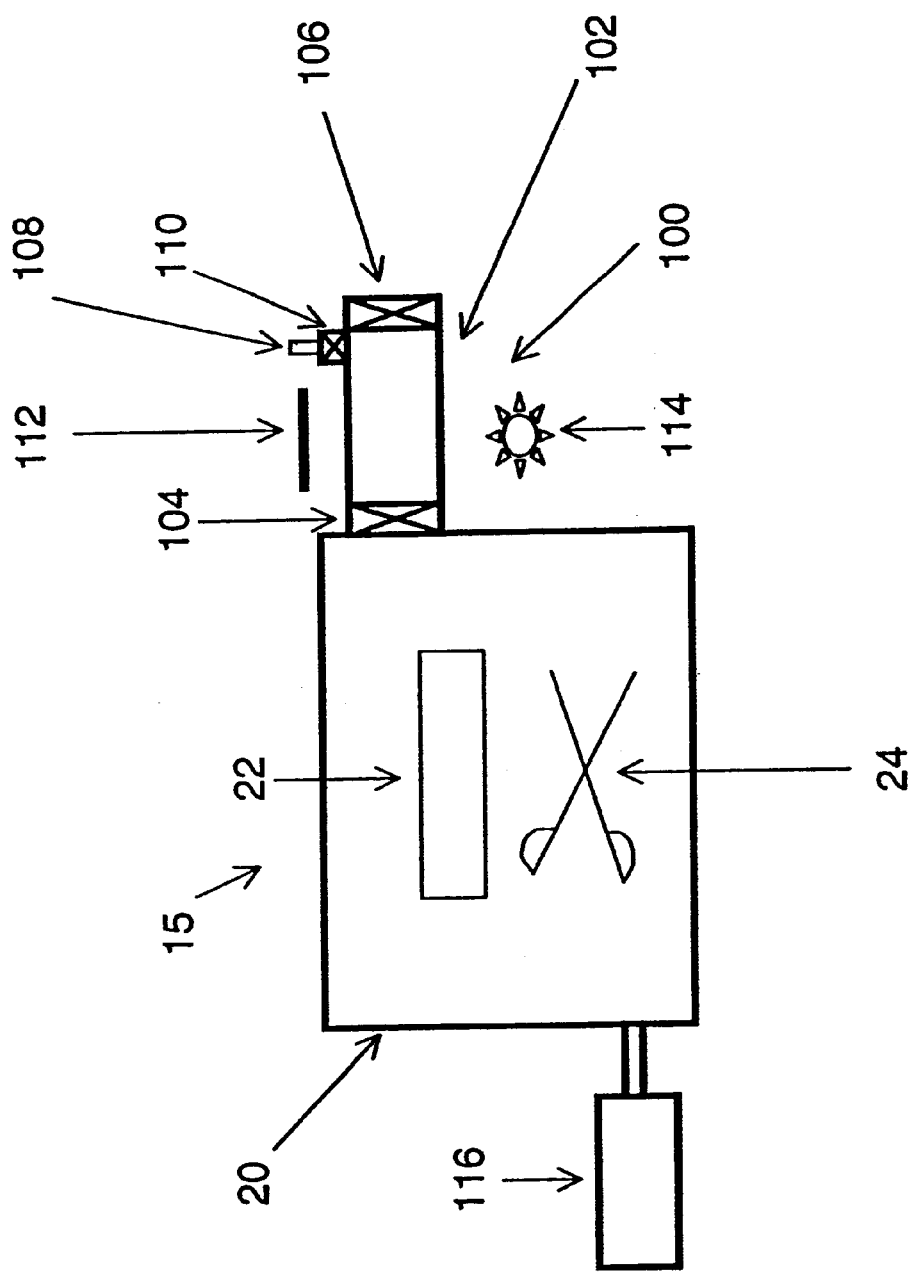
FIG. 14 is a schematic diagram of the apparatus according to another embodiment of the invention, which has a chemical source to facilitate the detection of soil.

FIG. 14 illustrates an apparatus 15 which contains a washing chamber 20 for washing or washing and sterilizing medical devices 24 and instruments 22 as previously described. Apparatus 15 also has an enclosure 102 coupled to chamber 20. Enclosure 102 is in controllable fluid communication with chamber 20. Preferably, chamber 20 and enclosure 102 is separated by a valve 104. Enclosure 102 is equipped with another valve 106 which can be connected to a drainage. A chemical source 108 is coupled to enclosure 102 through a valve 110. A chemical suitable for reacting with the soil in the washing liquid to generate a detectable signal, such as color, is stored in the chemical source. Examples of such chemical include, but not limited to, chloride ions reagent $(Hg(SCN)_2)$, OPA, albumin reagent, biuret reagent, and Microprotein-PR.

In use, valve 104 is opened and the washing, cleaning, or rinsing liquid in chamber 20 is allowed into enclosure 102 when a measurement is to be conducted. The amount of the washing liquid introduced into enclosure 102 can be controlled. Then valve 104 is closed and valve 110 is opened so that the chemical is introduced into enclosure 102. Once the chemical is introduced into the enclosure 102, chamber 20 and enclosure 102 should be totally isolated from each other so that no chemical will enter chamber 20. After the measurement is finished, the liquid in enclosure 102 is drained through valve 106. Enclosure 102 may have another clean washing liquid inlet (not shown) for introducing fresh washing liquid to clean enclosure 102. The amount of the chemical added to enclosure 102 is controlled. Preferably, concentration of the chemical in the washing liquid in the enclosure 102 is about the same in different measurements, so that intensity of the signal generated by the reaction between the chemical and the washing liquid will reflect only the content of soil in the washing liquid, but not affected by the chemical concentration itself.

A spectrophotometer 100 having a detector 112 and a light source 114 is provided to detect the signal generated by the chemical. The detector 112 and light source 114 can be placed inside or outside enclosure 102. In case they are located outside enclosure 102 as shown in FIG. 14, at least a portion of the wall of enclosure 102 should be transparent to the light from the light source 114 so that the light can travel through the body of the washing liquid in the enclosure and reach to detector 112. When the generated signal is a color, it can be observed visually, thus, human eyes can serve as a detector.

The structures as described previously with FIGS. 9–13 can be combined with the apparatus 15 of FIG. 14. Optionally, chamber 20 can be also connected to a vacuum pump or a vacuum source 116. When the cleaning is completed, vacuum can be applied to chamber 20 to facilitate the drying of the cleaned items 22 and 24. A sterilizing system can be also provide so that chamber 20 can be used as a sterilizing chamber. After the cleaning, sterilization can be conducted in the same chamber 20 without removing the instruments to be cleaned and sterilized. There are no limitations on the sterilization system to be used with the cleaning process of the present invention. Thus, any proper sterilization system can be used in combination with the cleaning process. If desired, cleaning and sterilization can be conducted simultaneously by using a combined cleaning and sterilizing solution, such as one with dissolved ozone or chlorine dioxide.

FIGS. 15a–15d show various apparatus according to other embodiments of the present invention. In these embodiments, a standard 120 covered with soil is provided. The purpose of the soil covered standard is to provide a standardized indication of the cleanness of the items to be cleaned during a cleaning precess. In other words, the soiled standard 120 will be cleaned simultaneously with the item or items to be cleaned, and the cleanness of the soil covered standard 120 will be monitored. A correlation between the cleanness of the item to be cleaned and the cleanness of the soil covered standard 120 for a particular apparatus configuration can be established through experiments. Thus, when the standard is cleaned to a certain degree, that will indicate a complete cleaning of the items to be cleaned has been achieved.

There are several advantages associated with the use of a soiled standard. For example, by using a soiled standard, one can focus on the standard for monitoring and the detection of soil removed from or remaining on the standard during a cleaning precess, thus the monitoring procedure can be standardized. The soil level and the cleaning efficiency of the standard 120 can be controlled. The standard 120 can be exposed to a cleaning environment which is equally efficient as or less efficient than that the items to be cleaned are exposed to, or standard 120 can be soiled more heavily than the items 22 and 24, so that when the standard is completely cleaned the items to be cleaned is guaranteed to be cleaned completely. Another option is to soil the standard 120 less heavily than the items 22 and 24 (here it means that the standard is covered with less soil), but put the standard 120 in a considerably less efficient cleaning environment, so that before the standard is cleaned the items to be cleaned will be completely cleaned. This option allows to reduce the soil level to which the detector exposes, thus, reducing the potential problems associated with the contamination of the detector surface by the soil. In general, conditions can be set up such that when the standard 120 is cleaned to certain level, the items 22 and 24 will be cleaned completely. This will allow the use of less sensitive detectors. The standard 120 can be covered with any proper soils such as those mentioned previously, or their combinations. Preferably, standard 120 is covered with the same soils as those contained in the items 22 and 24 to be cleaned. However, if desirable, the standard 120 can be covered with soil different from that of the items 22 and 24 to be cleaned. This will allow the use of certain soil on the standard and a preferred type of detection technology particularly suitable to that type of soil. Many other options are available as long as a proper correlation between the cleaning of the standard 120 and the cleaning of the items to be cleaned is established through experiments associated with particular apparatus configurations.

Figure 15A:
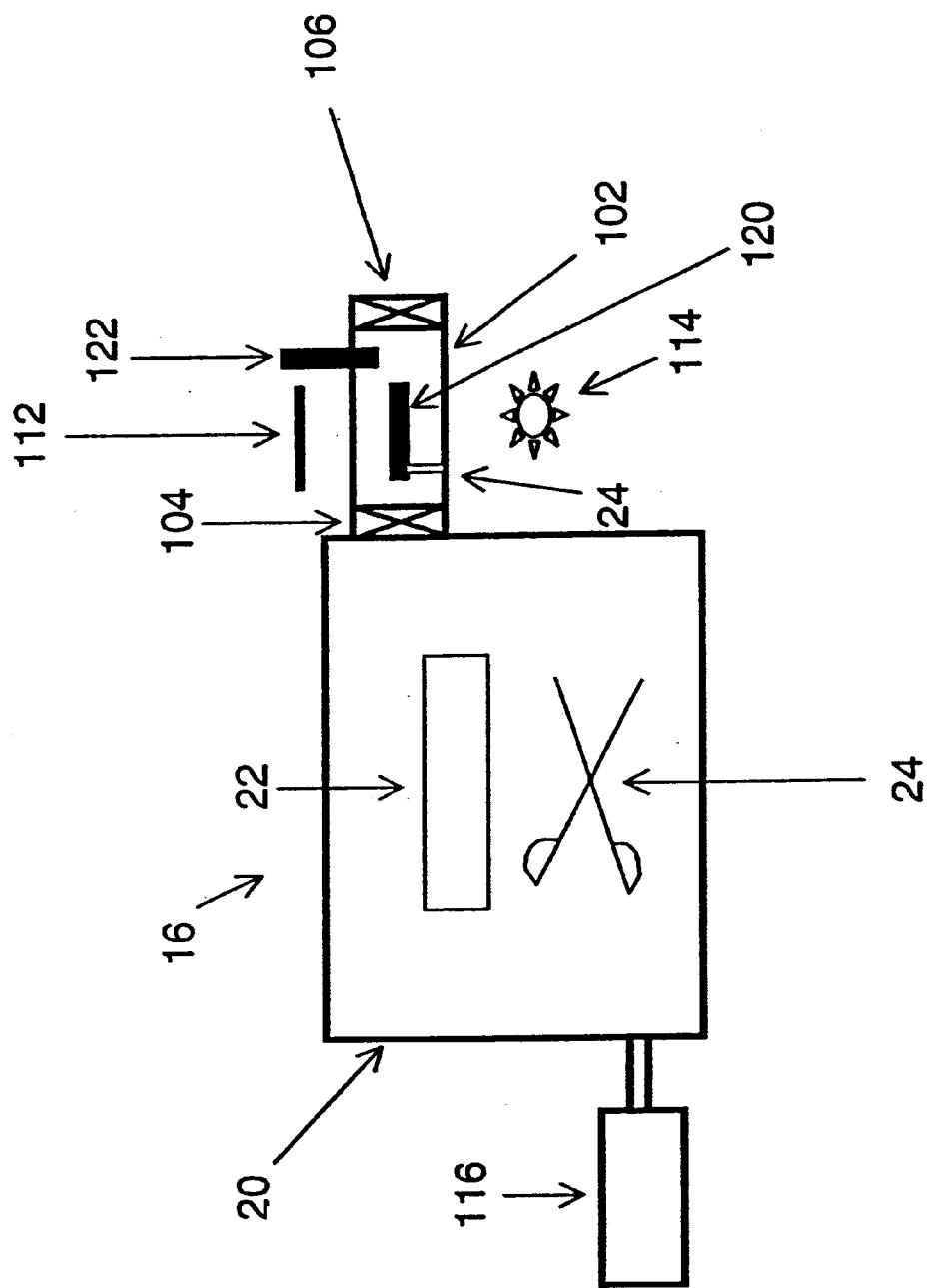

FIG. 15a illustrates an apparatus 16 with an soil covered standard 120 and a soil detector 122 positioned in an enclosure 102. Standard 120 can be any suitable surface covered with soil. For example, standard 120 can be a plate or a piece of suitable material preferably removably coupled to a support. Preferably, the connection between the standard 120 and the support 124 is made in such a way that the contact area of the standard is not soiled. There are several ways for controlling the cleaning efficiency of the standard 120 relative to that of the items 22 and 24. For example, valve 104 can be adjusted at different levels to control the fluid communication between chamber 20 and enclosure 102. A larger valve 104 will provide a better fluid communication, thus, the cleaning efficiency in chamber 20 and enclosure 102 will be closer to each other. Another option is to provide an adjustable agitation system in enclosure 102, or chamber 20, or both. By adjusting the agitation level, the cleaning efficiency in enclosure 102 or chamber 20 can be adjusted to a predetermined level. Detector 122 can be any suitable type, for example, it can be an electrode. Other parts of the apparatus 16 are similar to those of FIG. 14. In one embodiment, valve 104 is opened at a predetermined level during a cleaning process, and the soil level in the washing solution in the enclosure 102 is monitored with detector 122.

In another embodiment, an apparatus similar to that shown in FIG. 14 is used, the only difference is that a soil covered standard 120 is placed in enclosure 102. In this case standard 120 is made of material transparent to a predetermined wave length range. Preferably, standard 120 has a flat surface covered with soil which reacts with the chemical contained in the chemical source 108 (see FIG. 14) producing certain compound that absorbs light in a certain range of wave length. It is also possible to use light source 114 and spectrophotometer 112 alone without a chemical source.

FIG. 15b shows another embodiment, in which standard 120 is not placed in an enclosure, instead it is placed in an indentation. As shown in this figure, standard 120 is removably coupled to a support 122. Preferably, standard 120 is a flat plate with its surface covered with soil on one side or both sides. Support 122 is mounted on the wall of the indentation 130. Preferably, support 122 is movable, or standard can be coupled to support 122 at several positions, so that the position of standard 120 in the indentation 130 can be adjusted. Indentation 130 may have different shapes. For example, it can be an inclined gap with its two side walls 132 divergent from the wall of chamber 20 as shown in FIG. 15b. The two side walls 132 can also be made parallel to each other. If desired, indentation 130 may also have a surrounded side wall with only one end open to chamber 20. Because of the limited space, the cleaning efficiency in indentation 130 is lower than the area where the items 22 and 24 are placed, and the deeper and narrower the indentation 130, the less the cleaning efficiency is. Thus, the relative cleaning efficiency of standard 120 can be adjusted by placing it in different positions in the indentation 130. Agitation level in chamber 20 can also be used to adjust the cleaning efficiency.

Figure 15C:
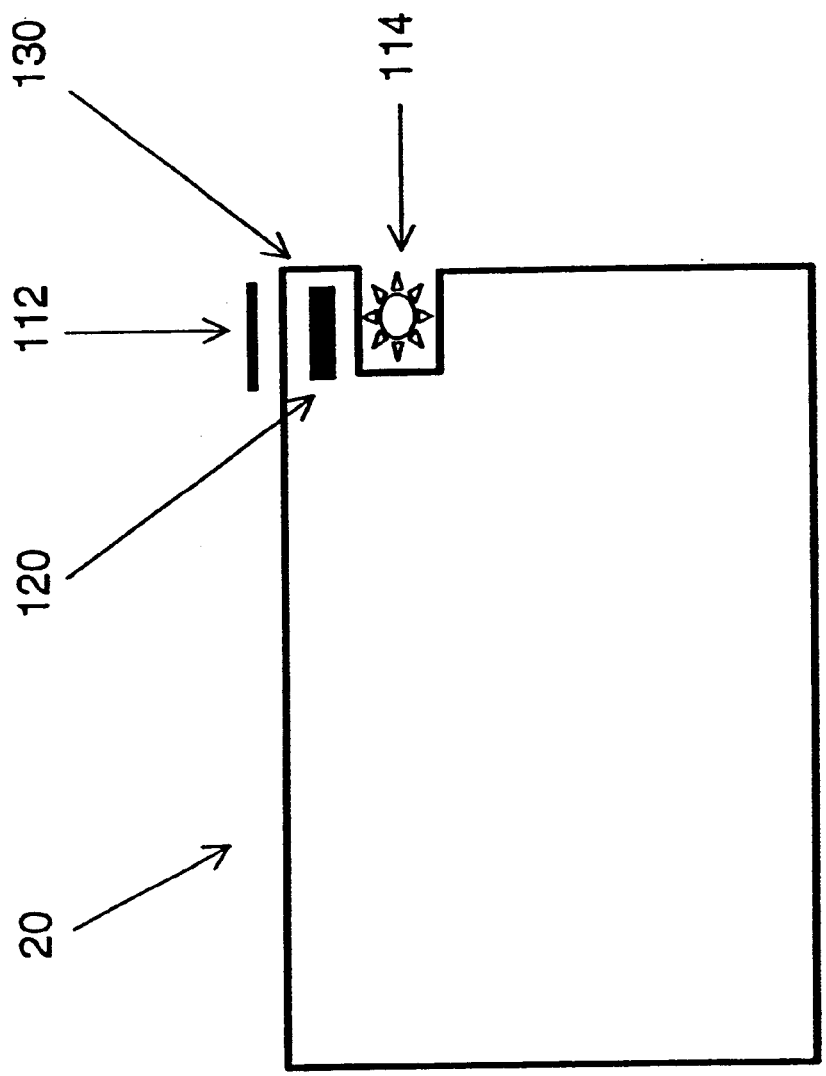
Figure 15D:
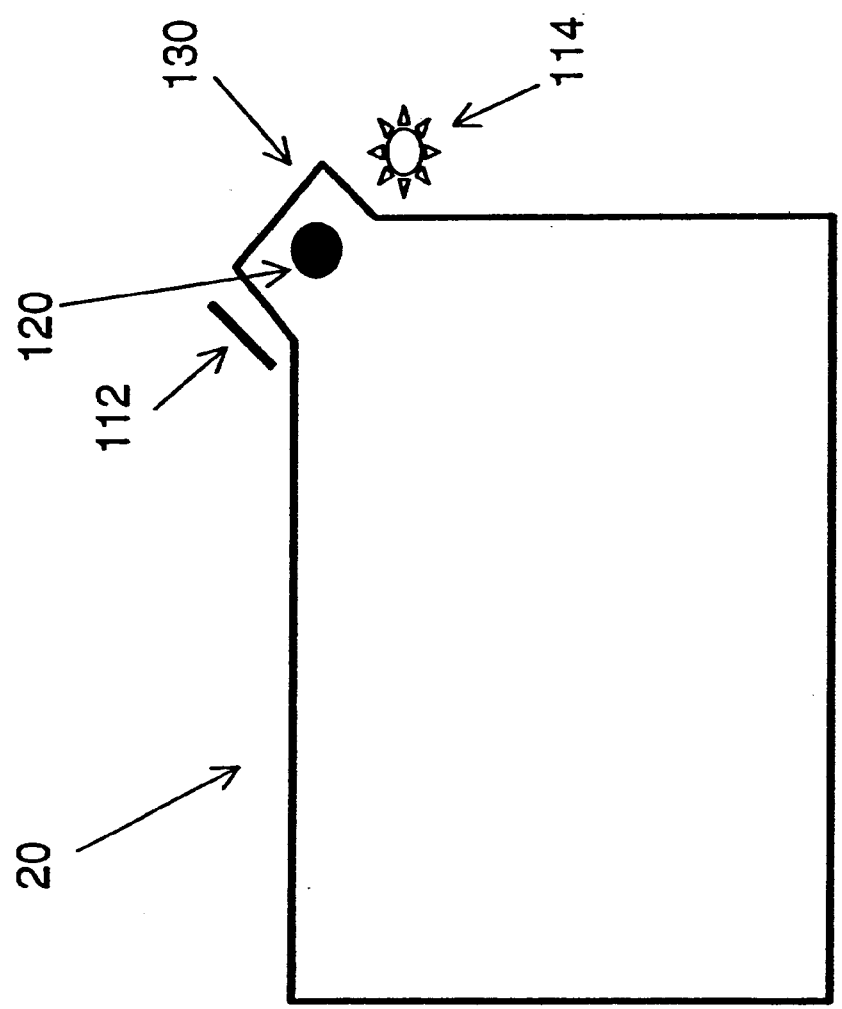

A light source 114 and a detector 112 are provided at two opposite sides of indentation 130. Side walls 132 are made of material transparent to the light from light source 114. Standard 120 is also made of material transparent to the light from light source 114. Thus, quartz is a suitable material for both the side walls 132 and the standard 120. FIGS. 15c and 15d illustrate two other configurations of the indentation 130. In the arrangement shown in FIG. 15c, indentation 130 is located at a corner of the chamber 20. Light source 114 is placed outside chamber 20 in a space next to indentation 130. In the arrangement shown in FIG. 15d, indentation 130 is also located at a corner of the chamber 20, but extruding outwardly. Light source 114 and detector 112 are placed outside chamber 20 in a space next to indentation 130. If the standard 120 to be used has a flat surface, the surface can be put in any proper orientation, vertical, horizontal, or with an angle. The light beam from the light source 114 can be vertical, horizontal, or any other angle.

The apparatus illustrated in FIGS. 15a–15d can be easily adapted to further include one or more other detectors of proper type, a vacuum pump or vacuum source for vacuum drying the items after cleaning, a sterilization system.

Generally, the embodiments of the apparatus of the invention illustrated in FIGS. 9–15d can employ one or more additional soil detectors. Soil detectors suitable for detecting protein are particularly useful additions. In such embodiments, it is preferable to use one more detectors for detecting inorganic soil in combination with an ultraviolet-visible spectroscopy detector suitable for detecting protein and other organic species. An example of the latter type of detector is a spectrophotometer employing a detection wavelength of 220 nm, one of the principle ultraviolet absorption wavelengths common to all proteins and many organic molecules found in the body. Many other wavelengths are also suitable, including 260, 265, and 280 nm. Another preferred soil detector combination employs one or more detectors along with a colorimetric autotitrator for detecting protein. Another preferred detector combination employs an ion-selective electrode detector and a turbidimetry detector. Combinations of detectors other than those listed may also be employed. All the apparatus illustrated in FIGS. 9–15d can employ a chamber 20 which also serves as a vacuum chamber, so that vacuum drying can be conducted in the chamber with a vacuum source. Various sterilization systems for liquid phase or vapor phase sterilization can be combined into the apparatus of the present invention illustrated in FIGS. 9–15d. When a long and narrow lumen device is to be cleaned and/or sterilized, chamber 20 can be further divided into two sub-chambers separated by a sealable interface with two open ends of the lumen positioned in the two sub-chambers separately. A pressure difference can be generated between the two sub-chambers, so that cleaning or sterilant fluid flows through the lumen. Thus, the lumen can be cleaned and sterilized more efficiently.

The foregoing examples are provided by way of illustration only and are not intended as a limitation of the present invention, many variations of which are possible without departing from the spirit and scope thereof.

What is claimed is:

1. An apparatus for monitoring a cleaning process for a medical instrument, comprising:

a cleaning chamber for receiving and cleaning the instrument with a cleaning liquid;

a soil detector coupled to the cleaning chamber and adapted to provide an indication of the amount of the soil on the instrument;

wherein the soil detector is at least partially controllably isolated from liquid in the chamber so that access to the detector by the cleaning liquid in the chamber is controllable during the cleaning process.

2. The apparatus of claim 1, wherein said soil detector is moveable and by moving the detector it can be made in or out of fluid communication with the chamber.

3. The apparatus of claim 1, wherein said soil detector comprises an electrode located in an enclosure, the enclosure is so coupled to the chamber that the cleaning liquid has controllable access to said enclosure.

4. An apparatus for monitoring a cleaning process for a medical instrument, comprising:

a cleaning chamber for receiving and cleaning the instrument; and at least a first soil detector and a second soil detector adapted to provide an indication of the amount of soil removed from or remained on the instrument, the first and second soil detector being placeable in fluid communication with the cleaning chamber, wherein the first soil detector and the second soil detector are not identical.

5. The apparatus of claim 4, wherein the first detector is located adjacent to an inlet of the cleaning chamber, the second detector is located adjacent to an outlet of the cleaning chamber.

6. The apparatus of claim 4, further comprising a second chamber in fluid communication with the cleaning chamber, and the first detector is located in the second chamber.

7. The apparatus of claim 4, wherein the first soil detector and the second soil detector detect different types of soil.

8. The apparatus according to any one of claims 1, and 4, wherein the detector is selected from the group consisting of ion-selective electrodes, conductivity, spectrophotometry, ion chromatography, capillary electrophoresis, high performance liquid chromatography, liquid chromatography, radioactivity, gravimetry, infra-red spectroscopy, potentiometry and turbidimetry.

9. The apparatus according to any one of claims 1, and 4, further comprising a vacuum pump connected to said chamber, wherein said chamber also functions as a vacuum chamber.

10. The Apparatus according to any one of claims 1, and 4, further comprising a sterilization system.

11. An apparatus for monitoring a cleaning process for a medical instrument, comprising:

a cleaning chamber for receiving and cleaning the instrument; and at least a first soil detector and a second soil detector adapted to provide an indication of the amount of soil removed from or remained on the instrument, the first and second soil detector being placeable in fluid communication with the cleaning chamber;

wherein the first soil detector is adapted to detect inorganic soil, and the second soil detector is adapted to detect organic soil.

12. An apparatus for monitoring a cleaning process for a medical instrument, comprising:
- a cleaning chamber for receiving and cleaning the instrument; and
- at least a first soil detector and a second soil detector adapted to provide an indication of the amount of soil removed from or remained on the instrument, the first and second soil detector being placeable in fluid communication with the cleaning chamber; and
- a vacuum pump connected to said chamber, wherein said chamber also functions as a vacuum chamber.

13. An apparatus for monitoring a cleaning process for a medical instrument, comprising:
- a cleaning chamber for receiving and cleaning the instrument;
- at least a first soil detector and a second soil detector adapted to provide an indication of the amount of soil removed from or remained on the instrument, the first and second soil detector being placeable in fluid communication with the cleaning chamber; and
- a second chamber in fluid communication with the cleaning chamber, and the first detector is located in the second chamber.

14. An apparatus for monitoring a cleaning process for a medical instrument, comprising:
- a cleaning chamber for receiving and cleaning the instrument with a cleaning liquid;
- a soil detector coupled to the cleaning chamber and adapted to provide an indication of the amount of the soil on the instrument;

wherein said soil detector is moveable and by moving the detector it can be made in or out of fluid communication with the chamber.

15. An apparatus for monitoring a cleaning process for a medical instrument, comprising:
- a cleaning chamber for receiving and cleaning the instrument with a cleaning liquid;
- a soil detector coupled to the cleaning chamber and adapted to provide an indication of the amount of the soil on the instrument;

wherein the soil detector comprises an electrode located in an enclosure, the enclosure is so coupled to the chamber that the cleaning liquid has controllable access to said enclosure.

16. An apparatus for monitoring a cleaning process for a medical instrument, comprising:
- a cleaning chamber for receiving and cleaning the instrument; and
- at least a first soil detector and a second soil detector adapted to provide an indication of the amount of soil removed from or remained on the instrument, the first and second soil detector being placeable in fluid communication with the cleaning chamber, wherein the first soil detector and the second soil detector detect different types of soil.

* * * * *

UNITED STATES PATENT AND TRADEMARK OFFICE
CERTIFICATE OF CORRECTION

PATENT NO. : 6,516,817 B2
DATED : February 11, 2003
INVENTOR(S) : Paul T. Jacobs, Jenn-Han Wang and Szu-Min Lin It is certified that error appears in the above-identified patent and that said Letters Patent is hereby corrected as shown below:

<u>Title page,</u>
Insert the following:
-- [73]  Assignee:  Ethicon, Inc., Sommerville, NJ (US) --

Signed and Sealed this

Twenty-ninth Day of July, 2003

JAMES E. ROGAN
*Director of the United States Patent and Trademark Office*